United States Patent [19]

Bander et al.

[11] Patent Number: 4,935,344

[45] Date of Patent: Jun. 19, 1990

[54] METHOD FOR CHARACTERIZING TYPES OF RENAL CARCINOMA AND PROGNOSIS

[75] Inventors: Neil H. Bander; Carlos Cordon-Cardo; Connie L. Finstad; Willet F. Whitmore, all of New York; Myron R. Melamed, Dobbs Ferry, all of N.Y.; Herbert F. Oettgen, New Canaan, Conn.; Lloyd J. Old, New York, N.Y.

[73] Assignee: Sloan-Kettering Institute for Cancer Research, New York, N.Y.

[21] Appl. No.: 837,531

[22] Filed: Mar. 7, 1986

Related U.S. Application Data

[63] Continuation-in-part of Ser. No. 605,603, Apr. 30, 1984, abandoned.

[51] Int. Cl.[5] .................. G01N 33/574; G01N 33/577
[52] U.S. Cl. ......................................... 435/7; 436/548; 436/817; 530/387; 530/809; 935/110
[58] Field of Search .................... 435/7; 436/520, 548, 436/813; 530/387, 808, 800

[56] References Cited

U.S. PATENT DOCUMENTS

| | | | |
|---|---|---|---|
| 4,579,827 | 4/1986 | Sakamoto et al. | 436/548 |
| 4,643,971 | 2/1987 | Fradet et al. | 435/948 |
| 4,650,756 | 3/1987 | Old et al. | 436/548 |
| 4,713,352 | 12/1987 | Bander et al. | 436/548 |

OTHER PUBLICATIONS

C. L. Finstad et al, *Chem. Abs.*, 102, 21940x, 1985.
Y. Fradet et al, *Proc. Natl. Acad. Sci* (U.S.A.), 81, 224–228, 1984.
A. N. Houghton et al, *Journ. Exp. Medicine*, 156, 1755–1766, 1982.
B. Ueda et al, *Proc. Natl. Acad. Sci.* (U.S.A.), 78, 5122–5126, 1981.
Finstad et al, *Proc. Natl. Acad. Sci.*, 82, 2955–2959, 1985.

*Primary Examiner*—Robert J. Warden
*Assistant Examiner*—David A. Saunders
*Attorney, Agent, or Firm*—John P. White

[57] ABSTRACT

Antigenic profiles of renal carcinoma specimens developed with panels of monoclonal antibodies derived from several different tissues serve as useful clinical indicators for cancer type, cancer subset as well as histiogenesis and prognosis indicators.

6 Claims, 1 Drawing Sheet

METHOD FOR CHARACTERIZING TYPES OF RENAL CARCINOMA AND PROGNOSIS

The invention was made in part with government support under CA 08748 awarded by the National Cancer Institute. The government has certain rights in this invention.

This application is a continuation-in-part of co-pending U.S. Pat. application Ser. No. 605,603 filed Apr. 30, 1984 and now abandoned.

The present invention relates to a method of using monoclonal antibodies and their antigenic specificities in identifying, characterizing as well as determining a prognosis for human renal cancers. This is a useful diagnostic tool in the detection and clinical prognosis of renal cancer as well as the study of the nature of renal cancer. Antigenic profiles offer insight into prognosis for renal cancer types.

Red blood cells, immunoflorescent, radioactive or enzymatic tagging agents can be bound to the highly specific antibodies using normal procedures, as required for indexing methods. Cytotoxic or cytostatic agents can also be bound to the highly specific antibodies to produce so called "magic bullet" type therapeutic agents which selectively destroy the cells with which the specific antibody binds.

BACKGROUND

In 1975 Köhler and Milstein introduced a procedure for the production of monoclonal antibodies (mAbs) using hybrid cells (hybridomas) which allows the production of almost unlimited quantities of antibodies of precise and reproducible specificity Nature 256:495 (1975). Conventional antisera, produced by immunizing animals with tumor cells or other antigens, contain a myriad of different antibodies differing in their specificity and properties, whereas hybridomas produce a single antibody with uniform characteristics. The Kohler-Millstein procedure entails the fusion of spleen cells from an immunized animal with an immortal myeloma cell line. From the fused cells (hybridomas), clones are selected that produce an antibody of the desired specificity. Each clone continues to produce only that one antibody. As hybridoma cells can be cultured indefinitely (or stored frozen in liquid nitrogen), a constant supply of antibody is assured.

Antibodies are proteins that have the ability to combine with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are *markers* by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available. Initial recognition of differentiation antigens came about through analysis of surface antigens of T-cell leukemias of the mouse and the description of the TL, Thy-1, and Lyt series of antigens. (Old, Lloyd J., Cancer Research, 41, 361–375, Feb. 1981). The analysis of these T-cell differentiation antigens was greatly simplified by the availability of normal T cells and B cells of mouse and man and is relatively advanced. (See U.S. Patent Nos. 4,361,549-550; 4,364,932-37 and 4,363,799 concerning mAb to Human T-cell antigens). Little is known about differentiation antigens displayed on normal and neoplastic cells belonging to other lineages.

This is due to the difficulty of obtaining a ready source of the appropriate normal cell type as well as the vagaries of the art of monoclonal antibodies. The preparation of hybrid cell lines can be successful or not depending on such experimental factors as nature of the innoculant, cell growth conditions, hybridization conditions etc. Thus it is not always possible to predict successful hybridoma preparation of one cell line although success may have been achieved with another cell line.

Progress in defining surface antigens on melanocytes was made possible by the recently discovered technique of culturing melanocytes from normal skin (Eisinger, et al., Proc. Nat'l. Acad. Sci. USA, 79 2018 (Mar. 1982). This method provides a renewable source of proliferating cells for the analysis of melanocyte differentiation antigens.

We recently described our initial analysis of cell surface antigens of human malignant melanoma identified by mouse monoclonal antibodies (mAbs) (Dippold et al. Proc. Natl. Acad. Sci. USA ["PNAS"] 77, 6114–6118 (1980)) hereby incorporated by reference. This invention relates to a comparable analysis of human renal cancer. Previous work is found in a co-pending patent application Ser. No. 297,814, now U.S. Pat. No. 4,650,756, issued Mar. 17, 1987 Monoclonal Antibodies To Cell Surface Antigens of Human Renal Cancer and Ser. No. 474,224, now abandoned Monoclonal Antibodies to Human Renal Cancer Antigens and Method. We also note a co-pending application based on Dippold et al., Supra 307,060, now U.S. Pat. No. 4,808,704, and a co-pending application on gastrointestinal mAbs (c26) 474,415, now U.S. Pat. No. 4,579,827; co-pending patent application Ser. No. 474,224, now abandoned, concerns renal mAb F23 and co-pending application Ser. No. 567,066, now U.S. Pat. No. 4,643,971, concerns bladder mAbs J143, T16, T23, T43, T87, T101, T110, T138, J233, JP165, Om5, and Om37. This application as to bladder mAb is based on a manuscript published as Fradet, Y. et al. Proc. Nat'l. Acad. Sci. U.S.A. 81:224, 1984. All the above documents are hereby incorporated by reference.

Seventeen monoclonal antibodies derived from fusions with spleen cells of mice immunized with established culture lines of renal cancers identified nine cell surface antigenic systems (Ueda, Ryuzo et al, Proc. Natl. Acad. Sci. USA, 78, 5122, Aug. 1981 and the subject of U.S. patent application Ser. No. 297,814, now U.S. Pat. No. 4,650,756, issued Mar. 17, 1987 hereby incorporated by reference). Six of the systems gp160, $S_{25}$, gp120r, gp120nr, gp115, and $V_1$ represented new antigens not previously described. The other three systems were related to HLA-A, -B, and -C heavy chain and A and B blood group antigens. The most restricted of the newly described antigens were gp160, $S_{25}$, gp140 and gp120r. These determinants are found only on cells of renal origin, both normal and malignant, and represent differentiation antigens of human kidney. In addition to the difference in the molecular weight of two of these antigens, gp160, $S_{25}$, and gp120r can be distinguished on the basis of differential expression on a panel of cultured renal cancers and normal kidney epithelium and fetal kidney cells. Glycoproteins bearing gp120r share a determinant with renal gp120nr (as indicated by sequential precipitations with monoclonal antibodies that detect gp120r and gp120nr), but gp120nr is found on a broader range of cell types, including fibroblasts and cell lines derived from ovarian, bladder, and colon cancers. The two other new systems, gp115 and $V_1$, have characteristics of broadly occurring differentiation antigens but can be distinguished from each other and from gp120nr by differences in molecular weight, heat stability ($V_1$ is a heat-stable determinant), and differential expression on cell types of diverse origin.

These systems can be used to characterize and study the nature of renal cancer. Thus, comparison of the $S_{25}$ and gp160 phenotypes of different renal cancer cell lines and cultures of normal kidney clearly distinguish these two systems.

The study of renal cancer Ueda, supra, co-pending Ser. No. 307,060, now U.S. Pat. No. 4,808,704, of melanoma (Dippold, et al Proc. Natl. Acad. Sci. USA 77, 6614–6118 (1980)), has generated a series of mouse Abs that defined 12 new systems of human cell surface antigens. Six of these had been identified as glycoproteins (gp95, gp150, gp160, gp120r, gp120nr, and gp115), three are heat-labile antigens that could not be immunoprecipitated from labeled cell extracts ($S_{25}$, $M_{19}$, and $R_8$), and three are heat-stable antigens, presumably glycolipids ($O_5$, $R_{24}$, and $V_1$). The use of a standard panel of cultured human cells allows ready comparisons of the reactivity of these monoclonal antibodies in direct serological tests and absorption analysis, and each of the antigenic systems has a distinct pattern of distribution on the cell panel, in terms of both qualitative and quantitative expression of antigens. On the basis of their distribution on different cell types, these 12 antigenic systems can be further classified into three groups: (i) those with characteristics of restricted differentiation antigens (e.g., the renal-specific gp160, $S_{25}$, and gp120r antigens and the $R_{24}$ antigen of melanoma and melanocytes), (ii) more broadly represented differentiation antigens (e.g., gp95, gp150, $M_{19}$, gp120nr, and $V_1$, and (iii) antigens expressed by every human cell type tested (e.g., $O_5$ species antigen).

It has also been found that the cell lines derived from stage I renal cancer (confined to the kidney) are gp160+, whereas cell lines from metastatic renal cancers are gp160−. Whether this indicates that cancer cells developing metastatic potential lose gp160 expression, or that gp160+ and gp160− renal cancers are derived from separate cell lineages is not determined; however, identifying the cell types in normal kidney that express gp160 and other antigens found on renal cancer should give information about the cellular origins of renal cancer.

These serological probes provided by the invention can identify kidney-specific antigens and are of particular interest in the study of kidney structure and function. In addition, some of the more broadly reacting antibodies are useful in studying other tumors—e.g. $V_1$ which distinguishes astrocytomas from melanomas.

The importance of parallel biochemical and serological characterizations of antigens identified by Abs is illustrated by the analysis of gp120r and gp120nr. Five Abs in this series immunoprecipitated a 120,000-dalton component from labeled extracts of SK-RC-7 renal cancer cells. Pre-clearing the extract with one of these Abs (AB $S_6$) removed the 120,000-dalton component identified by Ab $S_{23}$, indicating that the two Abs were reacting with the same molecule. However, the antigenic determinant detected by Ab $S_6$ and Ab $S_{23}$ can be distinguished in M-MHA tests and absorption analysis. Ab $S_{23}$ detected a kidney-specific antigen, whereas Ab $S_6$ reacted with a much broader range of cell types. These results can be explained by postulating two species of gp120 molecules, both carrying the epitope identified by Ab $S_6$ but only one with the epitope identified by Ab $S_{23}$. In agreement with this interpretation, supernatants after clearing with Ab $S_{23}$ still reacted with Ab $S_6$, even though no antigen precipitating with Ab $S_{23}$ remained. The epitope identified by Ab $S_{23}$ is found only on cells of renal origin, and, because of this restricted distribution, it is referred to as gp120r. The more widely distributed epitope has been designated "nr" to indicate its nonrestricted nature. gp120r and gp120nr may be the products of two separate genes or of a single gene whose product is modified in renal cells. Similar, although less striking, discrepancies in the cellular distribution of antigens identified by different monoclonal antibodies immunoprecipitating gp95 or gp150 molecules have also been explained on the basis of different epitopes being recognized (Dippold, et al. Proc. Natl. Sci. USA 77, 6114–6118 (1980)).

SUMMARY

Renal carcinomas can be typed with monoclonal antibodies leading to renal carcinoma subsets. Monoclonal antibodies can be used in a method to determine histiogenesis as well as prognosis of renal carcinoma subsets. Table A below summarizes characteristics of the six mAbs used in this study. None of the mAbs reacted with Lewis A. Lewis B, X, Y, A, B, or H blood group antigens. A detailed specificity analysis of these mAbs has been performed on a panel of 100 cultured cell lines (FIG. 1), fetal and adult tissues (Table IIA & B), and 86 tumor specimens (Table IIIA).

DETAILED DESCRIPTION OF THE DRAWING

Figure 1A:
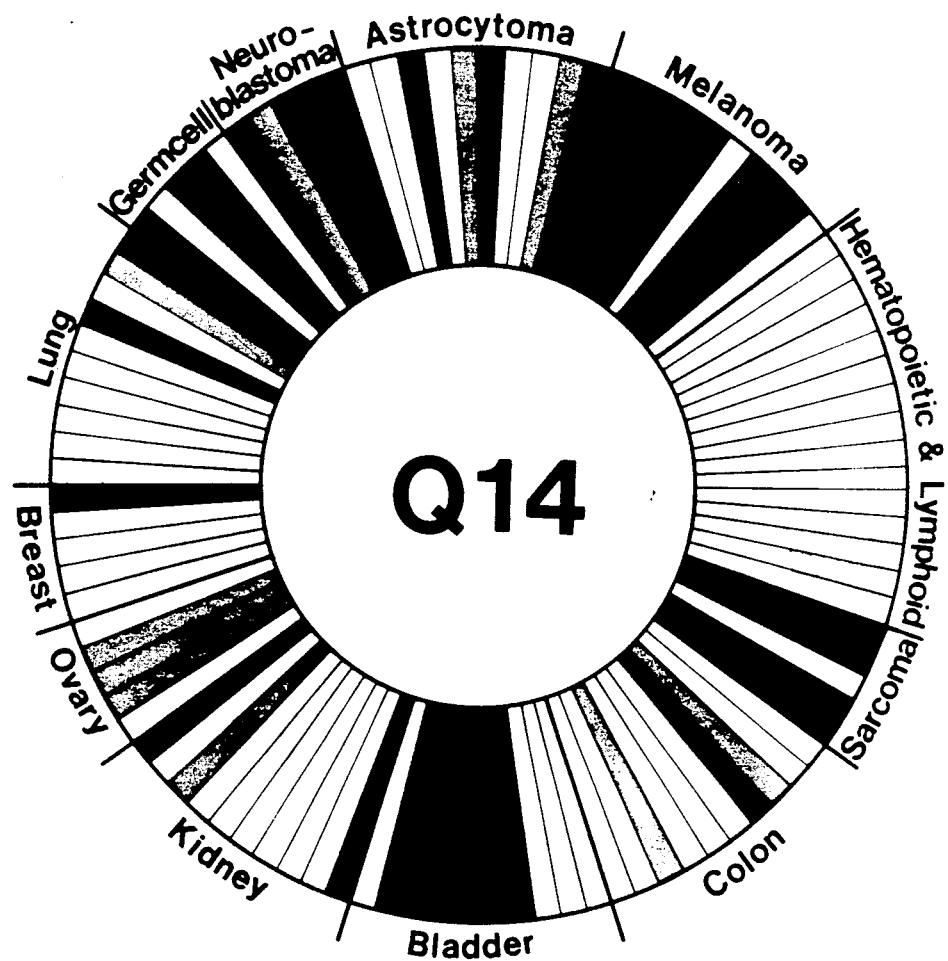
Figure 1B:
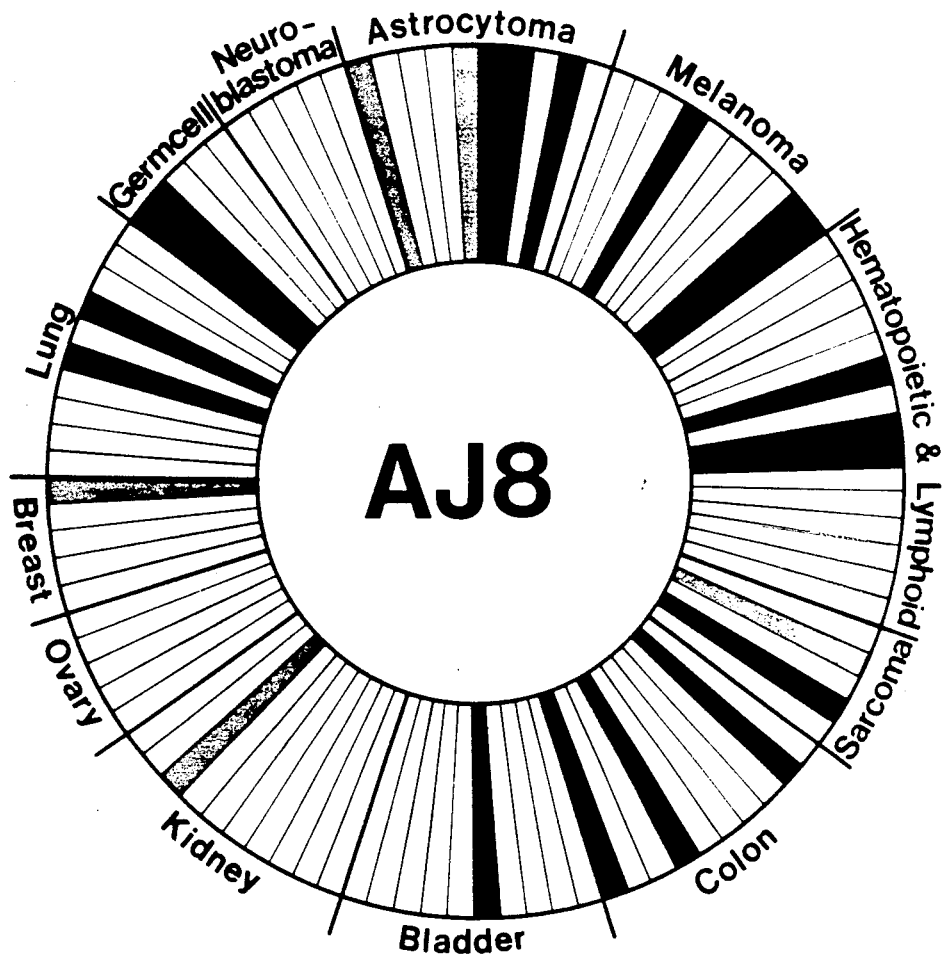
Figure 1C:
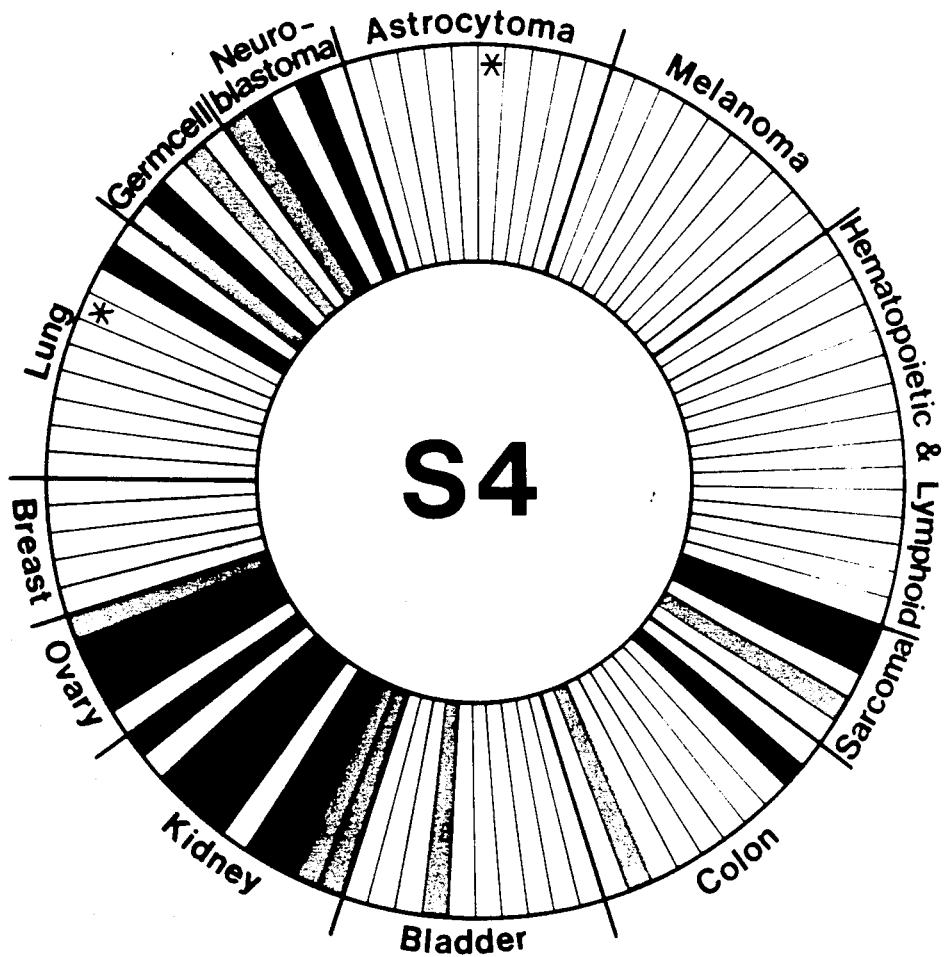
Figure 1D:
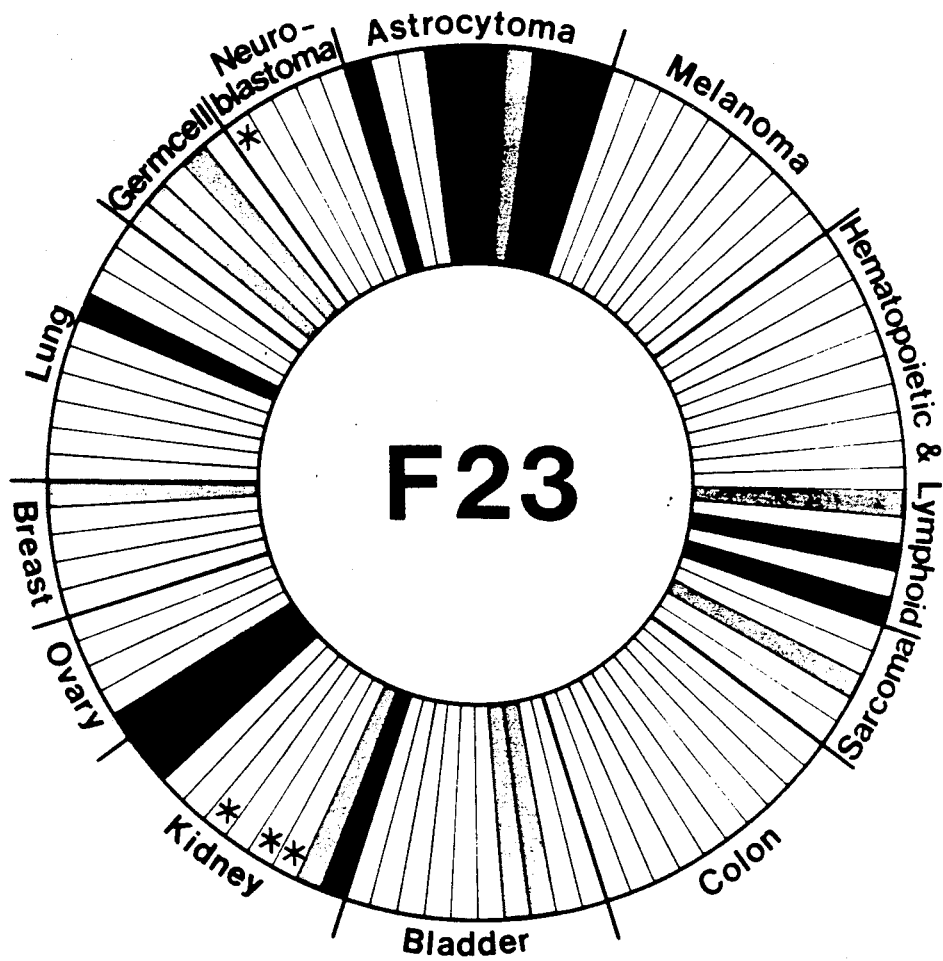
Figure 1E:
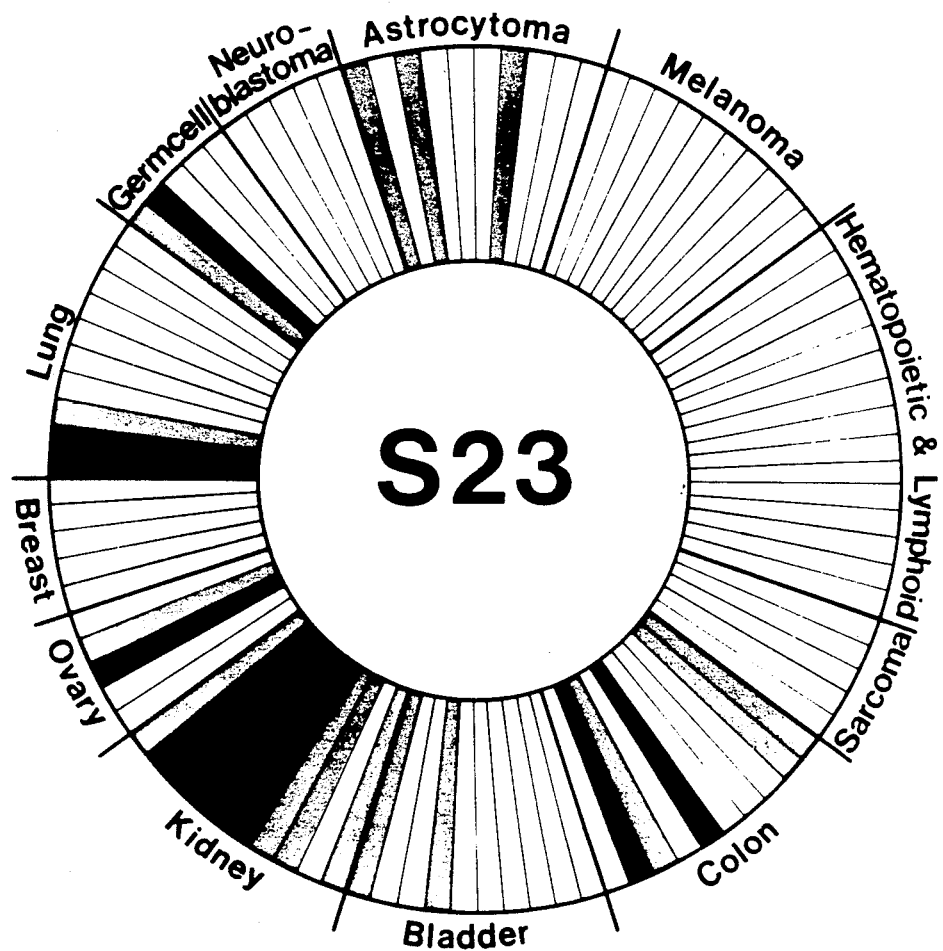
Figure 1F:
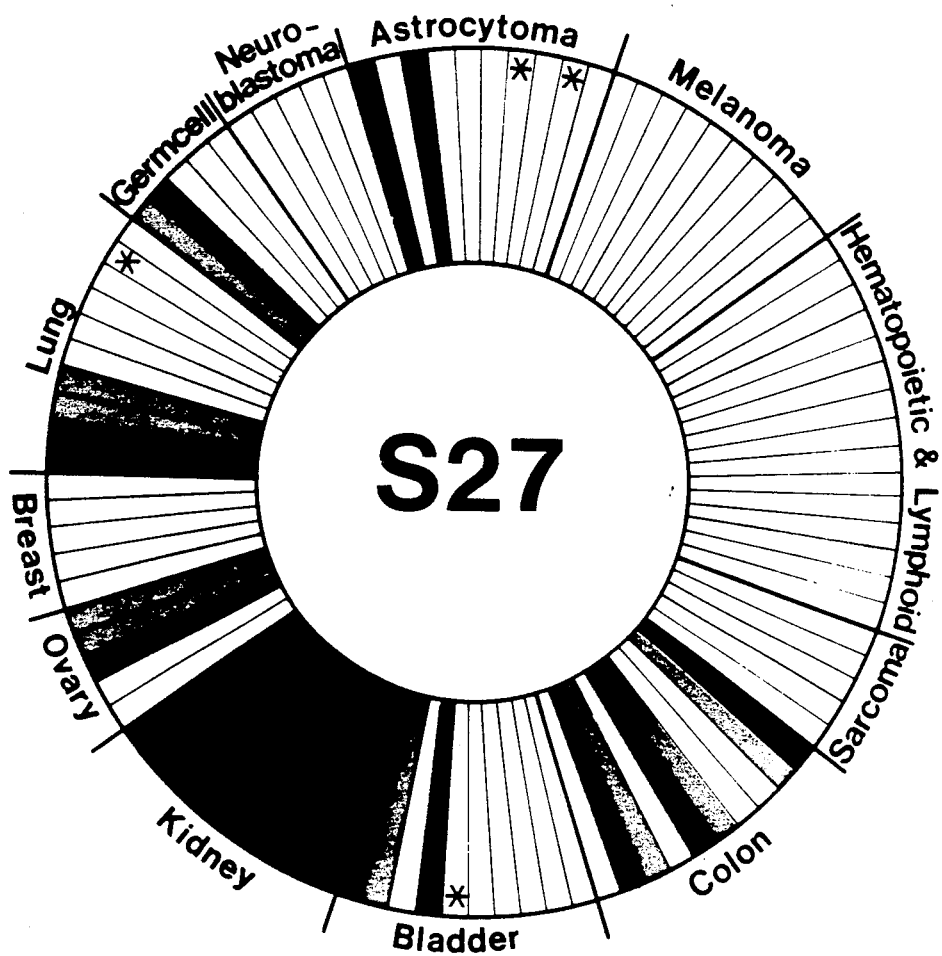
Figure 1G:
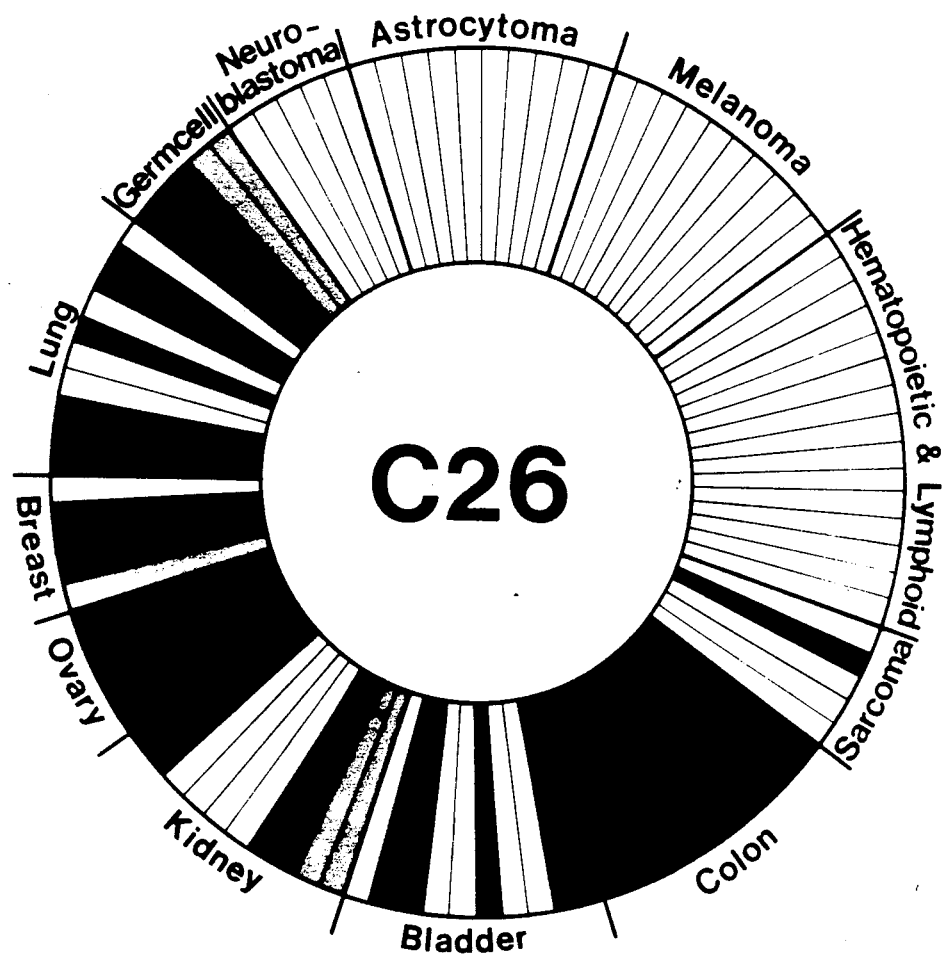
Figure 1H:
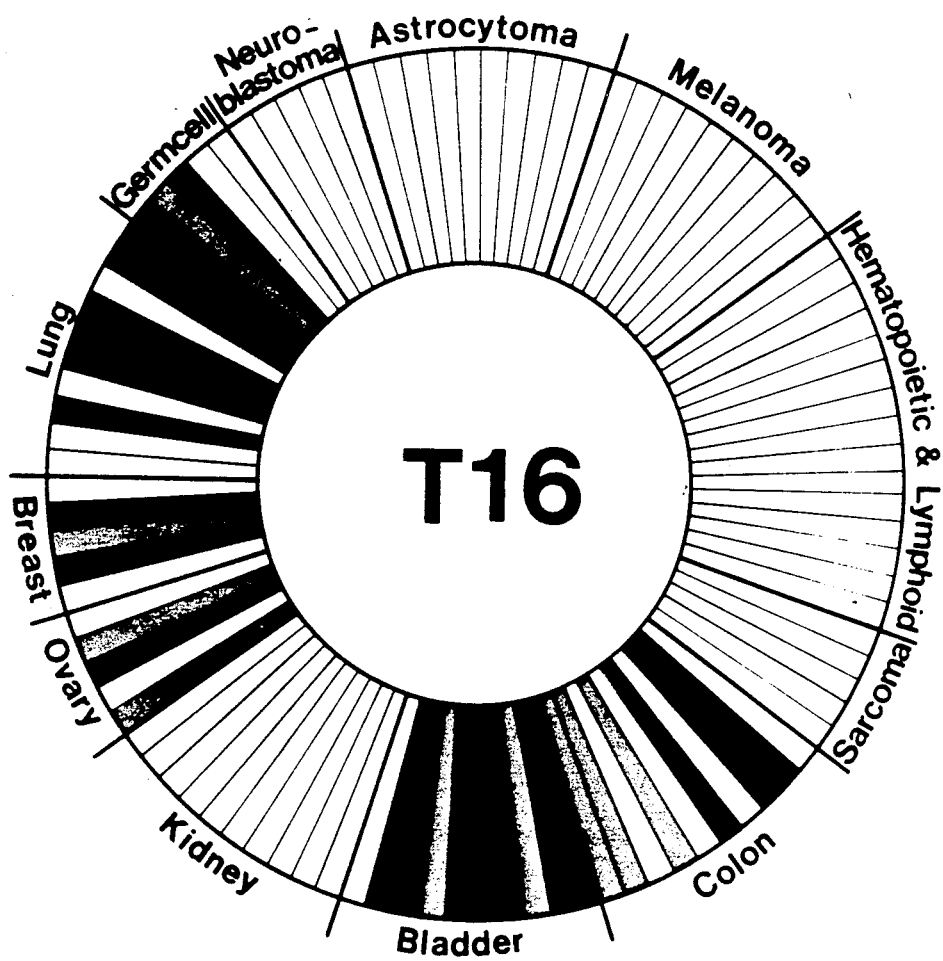
Figure 1I:
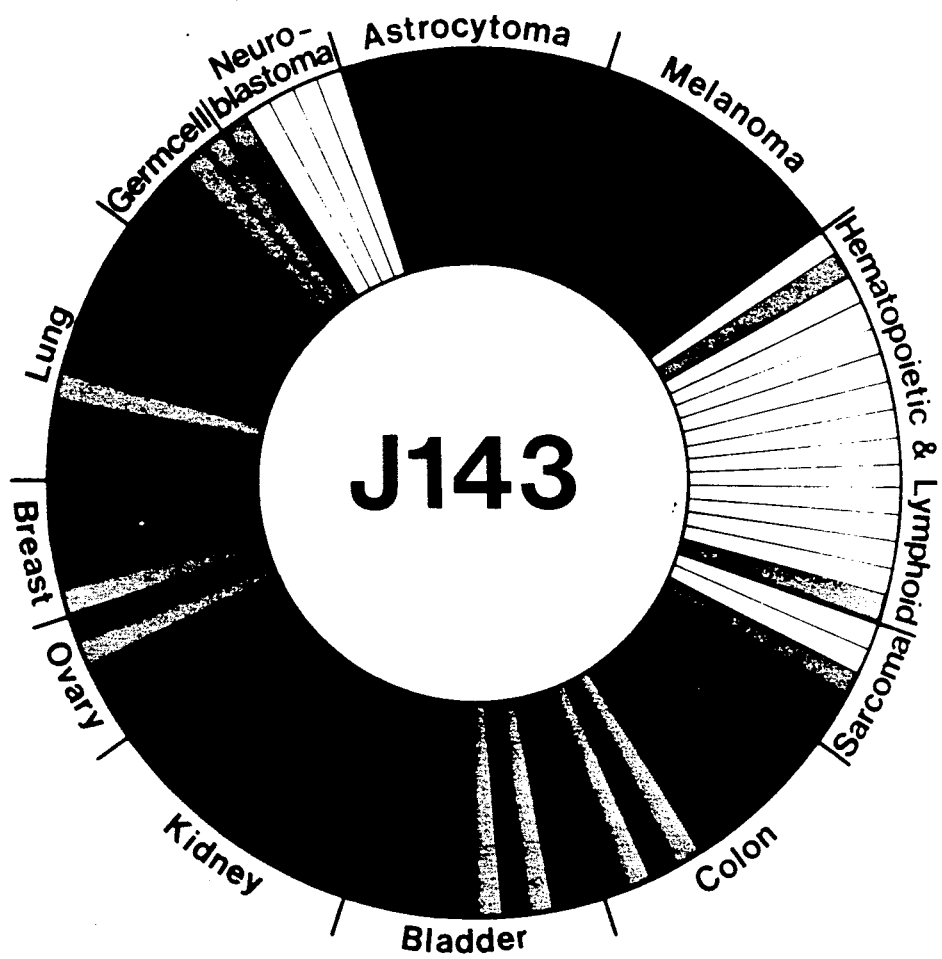
Figure 1J:
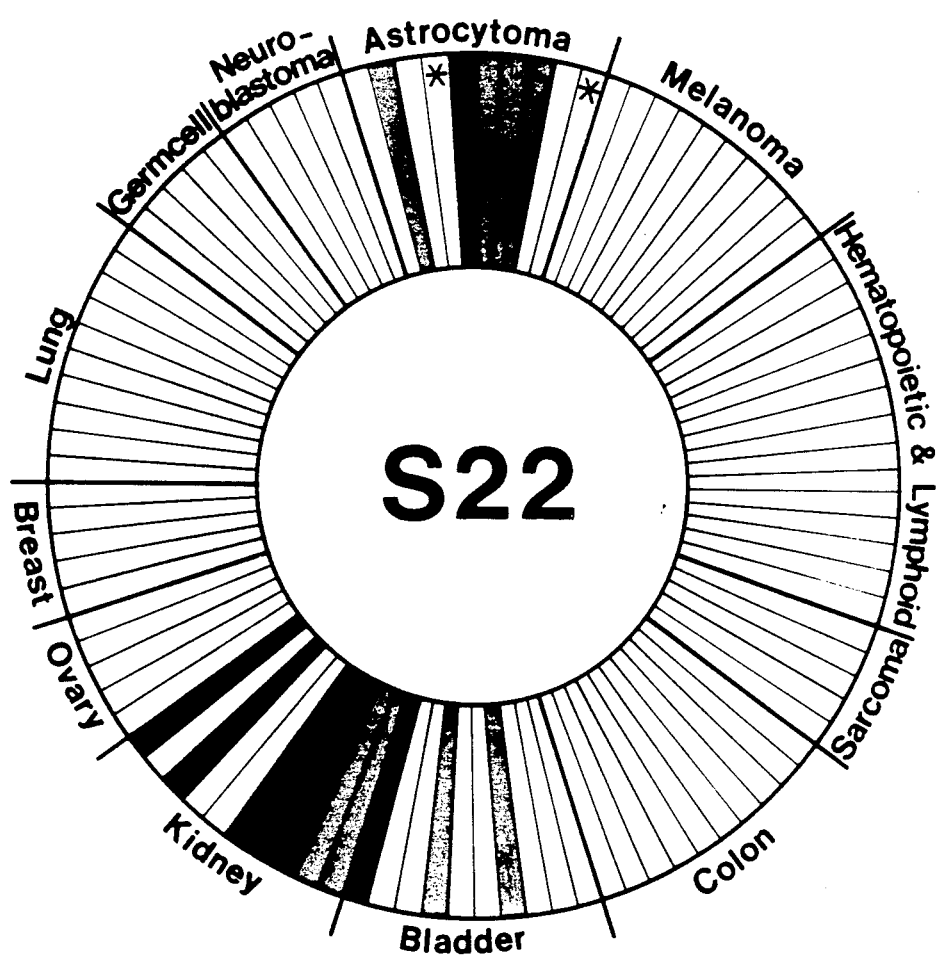
Figure 1K:
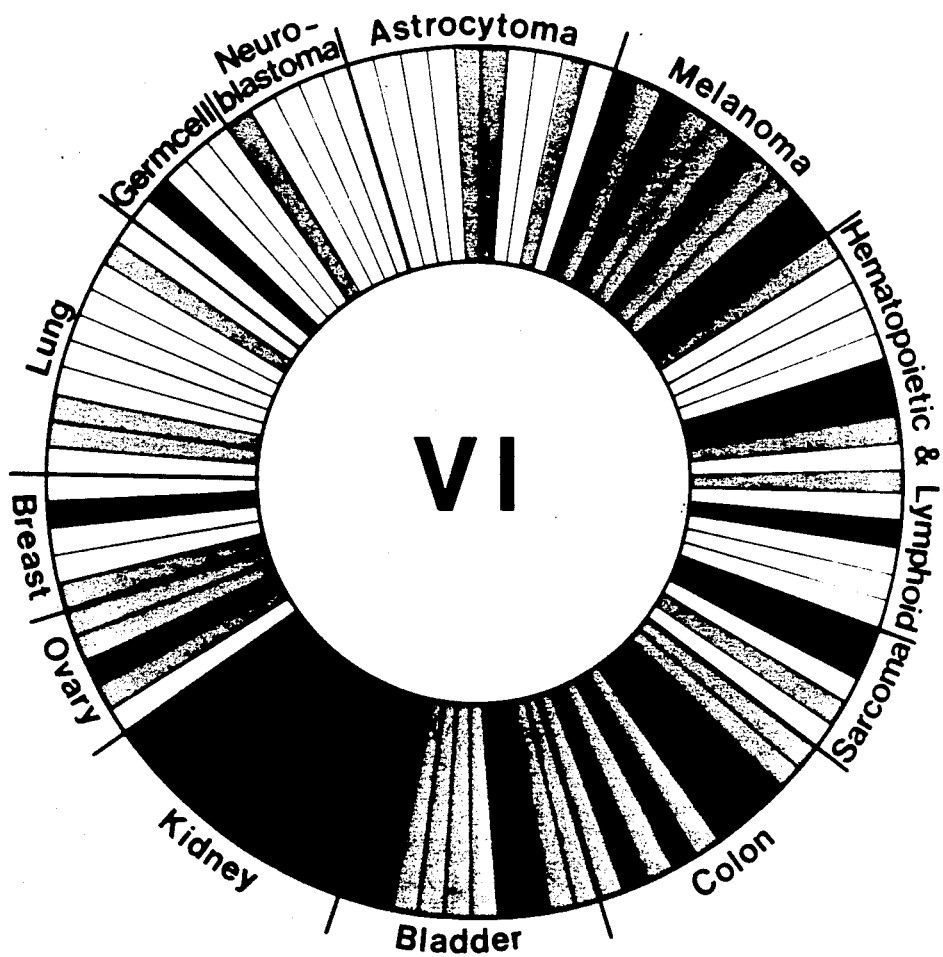

FIGS. 1a–1k. Schematic summary of serological reactivity of 11 mouse mAbs with cell surface antigens of 100 established human cancer lines.

Serological assays: mouse mixed hemadsorption assays and indirect immunofluorescence assays. Each segment of the circle represents an individual cell line (see below). M-MHA titers: dilution of antibody (serum or ascitic fluid from hybridoma bearing nu/nu mice) causing rosetting of 50% or more of target cells. Black segment: titer is greater than $1:10^5$ to $10^9$. Gray segment: titer is $1:5 \times 10^2$ to $10^5$. Clear segment: no reactions, titer is less than $1:5 \times 10^2$. Asterisk (#): 10% or less of the cell population showing rosetting at titer greater than $1:5 \times 10^2$. Indirect immunofluorescence assays with undiluted hybridoma supernatants gave parallel results with ++ to ++++ fluorescence corresponding to high M-MHA titers, + to ++ fluorescence to intermediate titers, and no fluorescence corresponding to titer 1:less than $5 \times 10^2$. Cell lines are listed clockwise and are the same for each circle. Starting at the top of the circle; Astrocytoma: SK-MG-1, -2, -4, -7, -8, -11, -13, -15, SK-MS, U251; Melanoma: SK-MEL-13, -19, -23, -28, -29, -31, -37, -113, -131, MeWo; Hematopoietic and Lymphocytic Cells: T45, CCRF-CEM, HPB-ALL, Molt 4, Hut 78, NALM 16, NALM 1, Daudi, SK-DHL-2, Ara 10, ML-1, K562, HL-60, KG-1, U937; Sarcoma: SK-ES-1, 5838, RD-2, SW 684, U-20S; Colon: HT-29, SW 403, SW 480, SW 620, SW 837, SW 1116, SW 1222, SW 1417, CaCo 2, SK-CO-10; Bladder: RT-4, SW 780, SW 800, 639V, 575A, T24, TCC-SUP, J'O.N., VM-CUB-2, 253J: Kidney: SK-RC-1, -2, -4, -7, -8, -10, -26, -28, -42, -45; Ovary: SK-OV-3, -4, -6, SW 626, 2774; Breast: AlAb, BT-20, CaMa, MCF-7, MDA-MB-157; Lung: SK-LC-1, -2, -5, -6, -8, -9, -10, -11, -12, CaLu 1; Germ Cell: Jeg 3, GCC-SV(c), 833K, Tera 2, Tera 1; Neuroblastoma: PNDW, LA-N-1s, SK-N-SH, SK-N-MC, SK-N-BE(2).

Description

TABLE A

Derivations and characterization of six mouse mAbs detecting cell surface antigens of human renal cancer

| Designation (Ig subclass) | Immunizing cell type | $M_r$ of antigen* | Chromosome assignment of locus coding for antigen* |
|---|---|---|---|
| mAb S4 (gamma 2a) | SK-RC-7 renal cancer | 160,000 (gp160) (1) | Not known |
| mAb F23 (gamma 2a) | Normal Kidney epithelium | 140,000 (gp140) | Chromosome 15 (6) |
| mAb S23 (gamma 1) | SK-RC-7 renal cancer | 120,000 (gp120) (1) | Chromosome 2+ (7) |
| mAb S27 (gamma 1) | SK-RC-7 renal cancer | 120,000 (gp120) (1) | Chromosome 2+ (7) |
| mAb S22 (gamma 1) | SK-RC-7 renal cancer | 115,000 (gp115) (1) | Not known |
| mAb V1 (gamma 1) | SK-RC-6 renal cancer | Heat stable (1) | Chromosome 12 (8) |

*References are shown in parentheses.
+Based on the finding that mAbS23 and mAbS27 detect epitopes on the ADA-BP [(Ref.(1)) Ueda, R., et al. (1981) Proc. Nat'. Acad. Sci. USA 78:5122–5126].
(6) Rettig, W. et al. (1984) Proc. Nat'l. Acad. Sci USA 81:6437.
(7) Herbschleb-Vogt, E., et al. (1981) Hum. Genet. 57:317.
(8) Dracopoli et al. (1984) Somatic Cell Mol. Genet. 10:475–481.

Techniques

Tissue Culture. The renal cancer cell lines (Ueda et al J. Exp. Med. 150, 564–589 (1979)) and tumor cell lines (Carey, et al Proc. Natl. Acad. Sci. USA 73, 3278–3282 (1976)) have been described. Methods for the short-term culture of normal kidney epithelium have also been described (Ueda (supra)). Fetal tissues were obtained from elective abortions. Normal adult tissues and tumor specimens were obtained from postmortem and/or surgical pathology specimens. Tissues were snap-frozen in liquid $N_2$. Leukemia and lymphoma cells were derived from fresh specimens and cryopreserved in culture medium with 10% dimethyl sulfoxide. Cultures were maintained in Eagle's minimal essential medium supplemented with 2 mM glutamine, 1% nonessential amino acids, 100 units of penicillin per ml, 1 microgram of streptomycin per ml, and 10% (vol/vol) fetal bovine serum. Cultures were regularly tested for mycoplasma, fungi, and bacteria, and contaminated cultures were discarded. SK-RC-7 serves as the immunizing cell line to derive mAbs S4, S22, S23, and S27 as well as $S_1$, $S_6$, $S_7$, $S_8$, $S_{11}$, $S_{21}$ and $S_{26}$. SK-RC-6 serves as the immunizing cell line to derive mAb $V_1$ and $V_2$. SK-RC-28 serves as the immunizing cell line to derive mAbs $M_1$ and $M_2$.

Serological Procedures. The mouse mixed hemadsorption assay (M-MHA) was performed by the method of Fagraeus et al. Immunology 9, 161–175 (1965), as modified to detect mouse antibody (Metzgar, R. S., et al. (1968) Cancer Res. 28:1366). Serological procedures for direct test and absorption analysis are described in Dippold et al (supra); Ueda et al (supra) and Carey et al (supra). Briefly, as described by Carey, Supra, cultured cells were harvested, washed and distributed to the wells (1000 cells per well) of 3040 microtest II plates (Falcon Plastics, Oxnard, Calif.) and the plates were incubated at 37° in a $CO_2$ incubator. Multiple plates were prepared for each test and examined in MHA assays at several different time intervals after cell passage to insure detection of surface antigens with variable expression.

Serum dilutions were prepared in phosphate-buffered saline (Pi/NaCl) containing 5% FCS. The medium was decanted from the test plates and 0.05 ml of each serum dilution was added to replicate wells. The plates were then incubated at room temperature for 45 min and washed three times with Pi/NaCl-FCS. Indicator sheep red blood cells were suspended in Pi/NaCl-FCS (0.2% vol/vol) and 0.1 ml aliquots were added to each well. The plates were again incubated at room temperature for 45 min, agitated gently, washed three times in Pi/-NaCl-FCS, and examined under a light microscope. Each well was scored for percent positive target cells, and for the intensity of the reaction. A cell was considered positive when ¼ or more of its perimeter was covered by indicator cells. For a well to be scored positive, 5% or more positive cells needed to be present. (This represents a stringent criteria as 1% positive cells in a well could usually be detected without question).

The absorption procedure according to Old et al. [Old, L.J., (1965) Cancer Res. 25:813] as decribed by Carey, Supra is as follows:

On the day of the absorption test, the serum to be examined was titrated against target cells by MHA and the dilution yielding 25% positive cells was determined. A dilution of serum two doubling dilutions below this end-point was prepared. One aliquot remained unabsorbed, while other aliquots were each mixed with an equal volume of packed cells. (In order to avoid possible enzymatic destruction of surface antigens, cultured cells used for absorption were harvested by mechanical scraping). Absorptions were carried out, with frequent mixing, first at room temperature for 45 min. and then on ice for an equal period. The absorbing cells were then removed by centrifugation, and the absorbed and unabsorbed sera were serially diluted and tested against the target cells.

Immunofluorescence Technique

Using methods established in the prior art, for example: Frozen sections (5 micrometer) of tissues were fixed 5 min in 3.7% formaldehyde in phosphate-buffered saline (PBS), washed and incubated for 1 hr with undiluted hybridoma culture supernatants. The slides were washed and incubated for 30 min with a 1:40 dilution of flurorscein conjugated goat anti-mouse Ig (Cappel Laboratories, Cochranville, Pa.), washed again and wet-mounted in 90% glycerol in PBS. (See Fradet, Y, et al. Proc. Nat'l. Acad. Sci. USA (1984) 81:224).

Peroxidase Technique

Using standard methods established in the prior art indirect immunoperoxidase analysis was performed with hybridoma supernatant and horseradish peroxidase-conjugated rabbit anti-mouse IgG (DAKO, Accurate Chemicals, Westbury, N.Y.) 1:86 Dilution. mAb reactivity with normal and malignant tissues was analyzed initially by immunoperoxidase analysis and positive reactions were confirmed by immunofluorescence tests.

Immunizations. (BALB/C×C57BL/6)F$_1$ female mice were immunized with established renal cancer cell line SK-RC-7, mAb F$_{23}$ (gamma 2a) was derived from immunizations with cultured normal human kidney epithelium. For the initial immunization, 1×10$^7$ renal cancer cells were injected subcutaneously without adjuvant. Subsequent immunizations were carried out at intervals of 3-4 weeks by intraperitoneal inoculation of 1×10$^7$ renal cancer cells. Immunized mice were sacrificed 3 days after the last immunization. The production and reactivity of mouse mAbs (S4, S23, S27, S22 and V) has been described (Ueda, PNAS, SUPRA). mAb F23 (gamma 2a) was derived from immunizations with cultured normal kidney epithelium. F23 is the subject of copending patent application Ser. No. 474,224 hereby incorporated by reference.

Derivation of Mouse Abs. The fusion of immune spleen cells with mouse myeloma MOPC-21 NS/1 cells was performed as described (Dippold et al (supra) and Kohler & Milstein, Nature (London) 236, 495-497 (1975) and Ueda et al. (1981) Proc. Nat'l. Acad. Sci. USA 78:5122. Fused cells (5-8×10$^5$) in 1 ml of selective medium containing hypoxanthine, aminopterin, and thymidine were added to wells of tissue culture plates (Costar no. 3524, 24 wells per plate). Hybridoma cultures were subcloned at least three times by limiting dilution on a feeder layer of 1-3×10$^5$ mouse peritoneal macrophages. Culture supernatants were monitored for antibody activity on a panel of cultured cells consisting of two renal cancer cell lines (including the immunizing line), AJ astrocytoma, SK-MEL-33 and -37 melanomas, Me-180 cervix cancer, WI-38 fetal cells, VERO adult and fetal kidney epithelium, and fetal brain cells. Antibody subclass was determined by double diffusion in agar with anti-Ig heavy chain specific reagents (Bionetics, Kensington, M.D.). Cultures of cloned hybridomas were injected subcutaneously into nu/nu mice (Swiss background) and were also stored in liquid nitrogen. Sera from mice with progressively growing tumors were collected, stored at −70° C., and used for serological and biochemical characterization. The mouse mixed hemadsorption assay (M-MHA) has been described (Ueda, et al., PNAS, Supra and Ueda et al., J. Exp. Med., Supra).

Immunoprecipitation Procedures. Cells were metabolically labeled with [$^3$H] glucosamine in complete Eagle's medium containing 15 uCi of [$^3$H] glucosamine (New England Nuclear; 30-60 Ci/mmol; 1 Ci=3.7×10$^{10}$ becquerels) per ml for 48 hr at 37° C.; the labeled cells were extracted with 0.5% Nonidet P-40 (NP-40) in Tris buffer as described (Ogata et al. Proc. Natl. Acad. Sci. USA 78, 770-774 (1981)) except that the 3M KCl treatment was omitted. Immunoprecipitation was carried out by mixing a portion of the cell extract (1×10$^5$ cpm) with 2 ul of mouse serum and 20 ul of rabbit anti-mouse Ig serum (Cappel Laboratories, Cochranville, Pa.) in Tris buffer). Immune complexes were isolated by using *Staphylococcus aureus* and analyzed by NaDodSO$_4$/ polyacrylamide gel electrophoresis as described (Dippold et al (supra)). [$^{35}$S] Methionine-labeled samples were immunoprecipitated in a similar manner, except that Sepharose-rabbit F (ab')$_2$ anti-mouse Ig was used for isolating the complexes. To determine the pI of the antigens, immunoprecipitates were examined by two-dimensional electrophoresis by the O-Farrell procedure (O'Farrell, P. H. Biol. Chem. 250, 4007-4021 (1975)) modified as described (Ogata, et al (supra)). From the five fusions of NS-1 myeloma with three different renal cancer cell lines, 17 antibody-producing clones were selected for detailed analysis (Table 1). The serological specificity of these antibodies was tested on a panel of 47 established cell lines [13 renal cancers, 5 melanomas, gliomas neuroblastomas, 15 epithelial cancers 5 B-cell lines K562 (an erythroid leukemia), 2 T-cell lines (MOLT-4 and T-45), and monkey kidney cells (VERO)]. In addition, the antibodies were tested against short-term cultures of normal kidney epithelium, fibroblasts, and fetal tissues (brain, fibroblasts, and kidney). Human, sheep, rat and bovine etythrocytes were also examined. In most cases, serological analysis consisted of both direct and absorption tests. See Table IA for serological analysis of representative monoclonal antibodies and Table IB for specific titers.

These serological studies in conjunction with immunochemical analysis defined nine distinct antigenic systems. Three systems (gp160, S$_{25}$, and gp120) were initially restricted to normal and malignant renal cells, three systems (gp120nr, gp115, and V$_1$) were more widely distributed, and three systems were identified as HLA-A, -B, -C heavy chain and A and B blood group antigens.

In frozen section (Table II) S4, S6, S22, S23, and S27 shown specificity for kidney tissue. Serological tests shows specificity for kidney tumor (Table IA and B).

Abbreviations: mAb, monoclonal antibody: ADA-BP, adenosine deaminase binding protein; M-MHA, mouse-mixed hemadsorption assay; gp160, gp140, and gp115, glycoproteins of Mr 160,000, 140,000, 120,000, and 115,000.

Antigenic Systems gp160 Antigenic System. Five Abs in this series (S$_4$, S$_7$, S$_{11}$, S$_{24}$, and M$_1$) identify a 160,000-dalton glycoprotein that showed a high degree of specificity for human kidney cells. gp160 is a rather basic component with pI 7.5. By M-MHA tests, gp160 could be demonstrated on all cultures of normal kidney epithelium, 2 of 3 cultures of fetal kidney, and 7 of 13 established lines of renal cancer (Table 2). These results were confirmed in absorption tests. No other cell type, normal or malignant, was initially found to express the gp160 antigen, including VERO, a cell line derived from monkey kidney.

In the initial analysis of mAbS4, reactivity was restricted to cultures of normal kidney and renal cancer (Ueda, R., et al. PNAS (1981) 78:5122). In the expanded panel of tissue culture lines shown in FIG. 1, gp160 expression was also detected on a portion of other types of epithelial cancers, and on neuroblastoma, choriocarcinoma (W. Rettig, unpublished observations) and sarcoma cell lines. In normal tissues (Table IIB), gp160 was found on epithelial cells of the fetal and adult golmerulus and proximal tubule; in the renal medulla, a positive diffuse staining was observed the interstitial matrix surrounding tubules and collecting ducts. Non-renal epithelial cells did not react with mAbS4 (Table IIB), but gp160 was found in vessels and interstitial matrix of tissues, including the placenta, myometrium, and fetal lung, gp160 was present in 16 of 20 renal cell carcinomas but was not detected in carcinoma cells of non-renal origin, melanomas, astrocytomas, leukemias, or lymphomas (Table IIIA)). However, gp160 was expressed by chondrosarcomas, osteogenic sarcomas, a spindle cell sarcoma and a mesothelioma.

$S_{25}$ Antigenic System. The antigen detected by Ab $S_{25}$ also is restricted to human cells of renal origin (Table 2). The $S_{25}$ determinant is heat liable, suggesting that it resides on a protein or glucoprotein, but Ab $S_{25}$ did not precipitate any detectable component from [$^{35}$S] methionine-labeled or [$^3$H] glucosamine-labeled SK-RC-7 cells. Comparison of the $S_{25}$ and the gp160 phenotypes of different renal cancer lines and cultures of normal kidney clearly distinguished these two systems. For example, SK-RC-6 and A-498 are gp160$^+$/$S_{25}^-$ and SK-RC-8 is gp160$^-$/$S_{25}^+$, whereas five of these cultures lacked $S_{25}$ expression.

gp120r and gp120nr Antigenic Systems. Five Abs ($S_{23}$, $S_{26}$, $S_{27}$, $S_6$, and $S_1$) immunoprecipitated a 120,000-dalton glycoprotein from [$^{35}$S] methionine- or [$^3$H] glucosamine-labeled lysates of SK-RC-7 cells. Analysis under reducing and nonreducing conditions gave the same results. The pIs of gp120 identified by prototype Ab $S_6$ and Ab $S_{23}$ were identical (4.9-5.2). A further indication of the relatedness of the gp120 components identified by these two groups of Abs came from sequential immunoprecipitation tests. Pretreatment of [$^3$H] glucosamine-labeled lysates of SK-RC-7 with Ab $S_6$ removed all antigen reactive with Ab $S_{23}$. In contrast, M-MHA tests and absorption analysis (Table 2) showed that these gp120 antibodies identified two serologically distinct gp120 epitopes that distinguish two classes of gp120 molecules: gp120r (restricted) and gp120nr (nonrestricted).

gp120r, identified by Ab $S_{23}$, had a highly restricted distribution, expression being limited to normal kidney epithelium and certain renal cancers. The other gp120 epitope, gp120nr, identified by Ab $S_6$ and Ab $S_{27}$, was found on a wide range of cultured cells including fetal and adult fibroblasts and cell lines derived from ovarian, bladder, and colon cancers. gp120r and gp120nr determinants differ in their expression on renal cancer cell lines: all cell lines carry the gp120nr epitope, whereas SK-RC-2, -21, -29, and Caki-1 lack gp120r determinants. The specificity of Ab $S_{23}$ for cells of renal origin resembles the reactivity of Ab $S_{25}$ and, most particularly, antibodies identifying the gp160 system. However, in addition to the molecular weight differences in the gp160 and gp120 antigens, these three kidney-specific antigenic systems can be distinguished on the basis of absorption analysis with selected normal or malignant kidney cells - e.g., SK-RC-6 and A-498 are gp160$^+$/$S_{25}^-$/gp120r$^+$; fetal kidney is gp160$^+$ or $^-$/$S_{25}^+$/gp120r$^-$.

$M_r$ 120,000 Glycoprotein (gp120; Designed S23 and S27) Antigenic Systems. mAbS23 and mAbS27 immunoprecipitated gp120 from metabolically labeled lysates of renal, bladder, colon, lung, and ovarian cancer cells (Ueda, et al. PNAS USA Supra: unpublished observations). Preclearing experiments showed that mAbS23 and mAbS27 detect different eptiopes on gp120, and Andy et al. (1984) J. Biol. Chem. 259:12844) have shown that gp120 is the adenosine deaminase binding protein (ADA-BP). In the initial survey of mAbs23 and mAbS27 with cultured cells (Ueda, R., et al. (1981) Proc. Nat'l. Acad. Sci. USA 78:5122-5126), S23 was found to be renal-restricted, while S27 was found on a wider range of cell types. With panel of cultured cells (FIG. 1), S23 was also found to be expressed by nonrenal cell types. S23 and S27 epitopes were detected on epithelial cells of fetal and adult proximal tubules and a portion of Henle's loop (Table IIB) and in 19 of 20 renal cancers (Table IIIA). In normal kidney tissue adjacent to kidney cancer in some specimens, the glomerulus and Bowman's space were also S23$^+$/S27$^+$. In nonrenal tissues, S27 was restricted to placental trophoblasts and prostatic epithelium, whereas S23 was more widely distributed—e.g., in epithelial cells of normal breast, colon, and lung (Table IIB). In tumors, the S23 epitope was also detected on a broader range of tumor types than the S27 epitope (Table III).

gp115 Antigenic System. Ab $S_{22}$ immunoprecipitated a 115,000-dalton glycoprotein from [$^3$H] glucosamine- or [$^{35}$S] methionine-labeled lysates of SK-RC-7 cells under both reduced and nonreduced conditions. In direct M-MHA tests, high reactivity (titers, 1-10,000×10$^{-3}$) was restricted to certain renal cancer cells and normal kidney epithelium. Absorption analysis, however, revealed that the gp115 antigen was expressed various cell types.

In the initial analysis of gp115, strong antigen expression was limited primarily to a subset of cultured renal cancers (Ueda et al. PNAS Supra). Low levels of antigen were detected on a number of other cultured cells, including normal kidney epithelium, by absorption analysis. In the expanded panel of cultured cells (FIG. 1), lines of bladder cancer and astrocytoma were also found to be gp115$^+$. gp115 expression in cultured cells is related to the time after cell passage; cells tested 1-2 days after plating showed much lower levels of antigen expression than did cells tested at 5 days. gp115 was not detected in any normal fetal or adult tissue (Table IIB) but was found in 10 of 20 renal cell carcinomas (Table IIIA). A weak outline staining of the cells of Bowman's capsulate has been observed in the adjacent normal renal tissue from some patients with renal cancer. In the panel of nonrenal cancer, one adrenal cortical carcinoma and one bladder transitional cell carcinomas were the only gp115$^+$ tumor types (Table IIIA).

gp140 antigenic system

MAb F23 recognizes another antigenic system gp140. $F_{23}$, is a gamma sub 2A (gamma 2A) immunoglobulin (Ig) antibody. MAb $S_4$ was in that same class of Ig while $S_{25}$, $S_{22}$, $S_{23}$, $S_6$, $S_{27}$, $V_1$ and $S_{21}$ belonged to immunoglobulin class gamma sub one (gamma $_1$) and $M_2$ and $S_8$ to Ig class mu(u). $F_{23}$ recognizes a new antigenic system on human renal cells-glycoprotein (gp) 140.

$F_{23}$ is derived from a hybridoma cell line wherein normal human renal epithlial cells are the immunogen. Yet $F_{23}$ monoclonal antibody recognize renal tumor antigens. This was an unexpected result.

As can be seen from Table I, $F_{23}$ recognizes human renal cancer cell lines. Of 25 cell lines tested, $F_{23}$ is positive for 19 of those. 33 human renal cell lines were studied. $F_{23}$ also recognizes some poorly differentiated renal carcinomas and some renal carcinomas with papillary differentiation with its best reaction with well differentiated renal carcinomas i.e. $F_{23}$ subsets renal carcinomas and can be used to assay for the malignant potential of renal tumors. Frozen renal carcinoma sections for over 20 different human specimens were tested as well. Comparison of frozen sections and tissue culture lines established from the same specimens reveals that for most antigens, expression is consistent in vivo and in vitro. See tables I & II.

$F_{23}$ also gives a positive reaction with all cell lines of normal kidney epithelium. However, $F_{23}$ did not react with normal human A, B or O erythrocytes by the absorption test. In frozen sections, $F_{23}$ reacted with normal kidney proximal tubule in fetal as well as adult specimens. (See tables)

FIG. 1 shows the distribution of gp140 in cultured cell lines. The antigen was detected on a proportion of cultured cancer cell lines of renal and nonrenal orgin. Cultures of normal kidney epithelium and fetal and adult fibroblasts were gp140+. In normal kidney, the expression of gp140 was limited to the proximal tubules in the fetal and adult renal cortex, fibrocytes between the tubules, in the renal medulla, and the fibrous capsule. In other tissues, mAbF23 reacted with connective tissue fibroblasts and fibrocytes. gp140 was detected in a proportion of tumors of renal and nonrenal origin, including a fibrosarcoma, chondrosarcomas and an osteogenic sarcoma (Table IIIA).

Some antigens may be either induced or suppressed in tissue culture. This characteristic must be determined for each antigen prior to extrapolating results between in vivo and in vitro systems.

Therefore $F_{23}$ mAb was added to the mAb panel for human renal cancer which to date includes the $F_{23}$, $M_1$, $M_2$, $S_1$, $S_4$, $S_6$, $S_7$, $S_8$, $S_{11}$, $S_{21}$, $S_{22}$, $S_{23}$, $S_{24}$, $S_{25}$, $S_{26}$, $S_{27}$, $V_1$ and $V_2$. This entire array of mAbs was used to diagnose renal cancer. A specimen tissue, body waste or fluid or exudate was contacted separately with each of the above mAbs in a screening test for a positive reaction. These mAbs are also useful in tissue typing - whether of normal or tumor tissue. $F_{23}$ was the invention relating to co-pending U.S. Pat. Ser. No. 474,224, now abandoned.

An alternate mAb for diagnosis and treatment of human renal cancer ("URO" panel) includes F23 as well. This panel comprises:

URO1—J143
URO2—S4
URO3—F23
URO4—S6/S27
URO5—T16
URO6—T110
EC1—T138

An alternate "URO" panel comprises:

URO1—J143
URO2—S4
URO3—F23
URO4—S27 (or S6)
URO5—T16
URO7—S22
URO8—F31
URO9—OM5
URO10—T43

This panel may or may not include URO6 (T110) as well. URO8 (F31) is the subject of a copending patent application Ser. No. 607,168, now U.S. Pat. Ser. No. 4,713,352, issued Dec. 15, 1987hereby incorporated by reference.

$V_1$Antigenic System. Ab $V_1$ did not immunoprecipitate any labeled component from [$^3$H] glucosamine- or [$^{35}$S] methionine-labled lysates of SK-RC-7 cells. Absorption tests indicated that the antigen is heat stable (5 mins. at 100° C.), suggesting that it is a glycolipid. Two features of the $V_1$ (Table IA) system are of particular interest: (a) it identifies a subset of bladder and breast cancers that do not express $V_1$, and (b) $V_1$ is not found on astrocytomas, whereas melanomas are strong $V_1$ expressors. This clear distinction between astrocytomas and malanoma, whose embryonic derivations are closely related, has not been seen with other Abs.

In recent test of cultured cells $V_1$ shows a broad pattern of reactivity (FIG. 1). In contrast, $V_1$ expression in normal and malignant tissues is highly restricted. In normal tissues, $V_1$ is localized to the zona fasciculata of the adrenal, Leydig cells of the testicle, and the theca of ovarian follicles (Tables IIB). In tumors, $V_1$expression was restricted to adrenal cortical carcinomas (Table IIIA).

HLA Heavy Chain. Ab $S_{21}$ immunoprecipitated a 45,000- and a 12,000-dalton component from [$^{35}$S] methionine-labeled SK-RC-7 lysates. The determinant detected by Ab $S_{21}$ in direct and absorption tests was present on virtually every human cell type with the exception of human erythrocytes (Table I). Of all the human cultured cells tested, the only cell lines not reactive with Ab $S_{21}$ in direct MHA tests were ME-180 and SK-MEL-19; the SK-MEL-19 melanoma cell line is known from previous work to express little or no HLA-A, -B, -C antigens. The molecular weights of the components precipitated by Ab $S_{21}$ and the results of the serological survey of human cells-indicated that Ab $S_{21}$ detected HLA but did not distinguish between a determinant on the heavy chain or on the gamma $_2$m chain. The fact that isolated human gamma $_2$m did not inhibit the reactivity of Ab $S_{21}$ suggests specificity for HLA heavy chain.

A and B Blood Group Antigens. The renal cancer line used for immunization expresses blood group B antigen on its cell surfaces i.e. SK-RC-7 is B+, while SK-RC-28 is A+. SK-RC-6 is derived from a type O individual and is negative for A and B reactivities. To detect Abs reacting with blood group antigens, hybridoma supernatants were screened for hemagglutinating antibody by using A, B, AB, or O erythrocytes. B (but not A) agglutinating activity was found in 4 of 462 supernatants from the anti-SK-RC-7(fusion) and A (but not B) agglutinating activity was found in 3 of 225 supernatants from the anti-SK-RC-28 fusion. No agglutination of type O erythrocytes was found in supernatants from anti-SK-RC-7, -28 or -6 fusions. Two monoclonal antibodies with hemagglutinin activity were derived from these fusions. The hemagglutination titer of Ab $M_2$(nu/nu serum) for A and AB erythrocytes was $10^{-4}$; B erythrocytes were not agglutinated by Ab $M_2$. The hemagglutination titler of Ab $S_8$ (nu/nu serum) for B and AB erythrocytes was $4 \times 10^{-5}$; A type erythrocytes were not agglutinated by Ab $S_8$.

Looking at the above results one can see that it is not always possible to predict successful hybridoma preparation of one cell line although success may have been achieved with another cell line. Any new cell line is impossible to predict because of the vagaries of the art of monoclonal antibodies. Preparation of hybrid cell lines can be successful or not depending on such experimental factors as nature of the innoculant, cell growth conditions, hybridization conditions and the like.

Normal proximal tubule cells express gp antigens at consistent levels (gp 160, gp120r and gp115) whereas only 5/31 tumors expressed all three antigens. 26 tumors did not express these antigens and 8 of the tumor cell lines tested were negative for gp140. In further differentiating normal versus malignant cells it is noted that when one of the gp antigens (160, 120r or 115) was present in a tumor levels of expression of the antigen ranged as high as 10,000 x normal. Results show antigen expression correlates with the malignant potential of these tumors.

In this present invention, MAbs S22, S23, S27 and S4 prepared from SK-RC-7 immunogen are now used to identify antigenically an clinically distinct subtypes of renal carcinoma using immunopathological techniques. These examples using specific mAb and renal carcinoma are illustrative of the invention and are not meant to limit it.

Frozen sections of 55 renal cancer (RC) specimens are typed with the four mAbs using standard immunoflourescence and peroxidase techniques. (Table IIIB) The mAbs detect four antigenic systems. gp120r, gp120nr and gp160 are glycoprotein differentiation antigens of proximal tubule (PT). gp115 is found only on renal cancer cells.

Subsets of RC can be identified on the basis of antigen expression at two levels. First, gp120nr expression separates a major group which is positive (51 in number) from a minor group which is negative (4 in number). Of gp120nr+RC, 41 (82%) express at least 2 of the PT differentiation markers consistent with the traditional view that RC is derived from PT. The 4 gp120nr−RC lack expression of the 3 PT markers (P less than .01) suggesting derivation from other parts of the nephron. Second, the gp120nr+group can be divided into eight subsets, defined by (+) or (−) expression of gp160, gp120r and gp115 (Table IV).

Contrary to the apparent coordinate lack of expression of these antigens in the gp120nr−subgroup, the gp120nr+RC demonstrate incoordinate, independent expression. Subsets of RC defined in this way may differ in their clinical course. 14/16 gp120r+/gp160+RC were localized to the kidney (p less than .001), whereas 9/9 gp120r−/gp160−tumors were disseminated (p less than .01) and developed at an earlier median age (44 vs. 57 years, ( p less than .01). These mAbs are useful in defining the histiogenesis, diagnosis and prognosis of RC subsets.

TABLE IV

| | gp 120nr+ Subsets | | | | | | | |
|---|---|---|---|---|---|---|---|---|
| gp 160 type | + | + | + | − | − | + | − | − |
| gp 115 type | + | − | + | + | + | − | − | − |
| gp 120r type | + | − | − | − | + | + | − | + |

The above examples are for illustrative purposes only and are not meant to limit the scope of the invention. It is obvious that the invention also encompasses all monoclonal antibodies and RC possessing the same characteristics as described herein. The examples do not limit the invention especially with respect to substantially functional equivalents of hybridomas, monoclonal antibodies, RC, cell lines and methods described and claimed herein.

Changes in cell antigens are associated with different stages of differentiation and different stages of cancer. Thus this invention technique defines cell antigens associated with differentiation and cancer of the kidney and its associated tubules.

This study provides a detailed specificity analysis of six mouse mAbs generated against cultured normal or malignant kidney cells. The initial analysis of two of these mAbs, mAbS4 and mAbS23, using a cultured cell panel suggested that they defined kidney-specific glycoproteins (Ueda, R., et al., (1981) Proc. Nat'l. Acad. Sci. USA 78:5122–5126). However, with an expanded cultured cell panel, it is clear that the antigens detected by mAbS4 and mAbS23 are expressed by other cell types, and tests with normal and malignant tissues lead to the same conclusion. In general, there is a good correlation between antigen expression by cultured versus noncultured cells, although exceptions can be noted. V1 is particularly striking in this regard. With the cultured cell panel, V1 is found on a wide range of different cell types, whereas in fresh tissues, V1 expression is restricted to the ovary, testis, and adrenal gland. Other antibodies with broad reactivity for cultured cells but with limited or no reactivity with fresh tissue have been found (Fradet, Y., et al. (1984) Proc. Nat'l. Acad. Sci. USA 81:224–228), and a possible explanation for this is that levels of these antigens are proliferation-related and are higher on rapidly dividing cells. However, this would not explain restricted expression of V1 in endocrine organs.

Andy et al. ((1984) J. Biol. Chem. 259 : 12844–12849) have shown that the gp120 molecule detected by mAbS27 and mABS23 is ADA-BP and that these mAbs identify distinct epitopes on ADA-BP. Past work with polyvalent antibody to ADA-BP has shown its presence in kidney, liver, lung, colon, spleen, and placenta, as well as fibroblasts and leukocytes (Schrader, W.P., et al., (1979) J. Biol. Chem. 154:11958–11963; Trotta, P.P. (1982) Biochemistry 21:4014–4023; Andy, R.J., et at. (1982) J. Biol. Chem. 257:7922–7925). ADA-BP also occurs in the body fluids such as serum, saliva, and urine. The tissue distribution of antigen recognized by mAbS23 follows this general pattern, but the ADA-BP epitope detected by mAbS27 has a more restricted tissue distribution. The discordance between the reactivity of mAbS23 and mAbS27 could be related to differences in affinities of these two mAbs or to differences in the accessibility or presence of S23/S27 epitopes in various cells and tissues. With regard to ADA-BP in tumors, there are number of conflicting observations in the literature. ADA-BP has been reported to be present (ten Kate, J., et al., (1984) Cancer Res. 44:4688–4692) or absent (Trotta, P.P., et al. (1978) Biochemistry, 17:270–278) in tumors arising in ADA-BP+tissues. As shown in Table III, not all cancers arising in S23+tissues express the S23 epitope, and S23+cancers (e.g., ovarian cancer) can have their origin in S23−tissues. Thus, ADA-BP expression, like other differentiation traits, provides a means to divide cancers of similar origin into subsets. The availability of mAbs to ADA-BP should facilitate further study of ADA-BP in cancers and determine whether ADA-BP expression can be correlated with any biological features of the tumor.

Four of the mAbs in the series reacted with separate regions of the nephron. S4 identifies epithelial cells in the glomerulus, S4/F23/S23/S27 react with proximal tubule cells, and S23/S27 identify portions of Henle's loop. In the fetal kidney, S4 marks the emerging glomerular tuft and proximal tubules, and S23/S27 mark the anterior region of the S-shaped structure that develops into the proximal tubule; F23 condenses around the expanding progenitor proximal tubule. Cordon-Cardo et al. ((1984) J. Histochem. Cytochem. 32:1035–1040) have selected a panel of mouse mAbs (including mAbS4, mAF23, mAbs27, and mAbs indentifying the distal tubule, collecting duct, and urothlium) that permits a serological dissection of the domains of the urinary system.

Evidence indicates that most renal cell carcinomas arise in cells of the proximal tubules (Riopelle, J.L., (1951) Cancer 4:789–802; and Wallace, A.C., et al.

(1972) Cancer 29:977-981) and, thus, would be expected to share the S4/F23 /S23/S27 phenotype of proximal tubular cells. Renal cancers arising in othe areas of the nephron would lack expression of these antigens (Wallace, A.C., et al. (1972).Cancer 29:977-981; Holthofer, H., et al. (1983) Lab. Invest. 49:317-326; and Gown, A.M., et al. (1984) Am. J. Pathol 114:309-321). As shown in Table III and Table V, distinct subsets of renal cancer can be defined by their antigenic phenotype. Some antigens (e.g., S23/S27) are expressed by virtually all renal cell carcinomas, whereas others (e.g., S4/F23/S22) are expressed by only a proportion of renal cancers. The significance of renal cancer subsets that lack expression of one or more tubule differentiation antigens needs to be assessed. Antigen loss could account for these tumor phenotypes or, as has been discussed in the case of melanoma (Houghton, A.N., et al., (1982) J. Exp. Med. 156:1755-1766), such tumor phenotypes could reflect a similar preexisting (but not recognized) cell type in the normal progenitor population. In addition to the subsetting or renal cancers by reactions with mAbs, cell populations in individual renal cancers show considerable heterogeneity in antigen expression, particularly in the case of F23, S23, and S22. Phenotypic and genotypic heterogeneity is a characteristic of virtually all animal and human cancers, and antigenic heterogeneity is one manifestation of this property of cancer cells. Evidence from experimental systems suggests that heterogeneity in surface antigen expression in tumor cells may result from stable, presumably genetic changes as well as from reversible variation in the cell population (Heppner, G. H., et al., (1983) Cancer Metastasis Rev. 2:5-23). If a stable genetic basis for antigen variation is involved and if this property accompanies altered cellular behavior, one might expect to find a difference in the surface phenotype of primary and metastatic renal tumor cells in the same patient. Thus far, our studies have not revealed consistent differences in antigen expression in primary verus metastatic tumors.

The antibodies and methods discussed above subset the nephron and subset renal cancers. These methods are clinically useful to diagnose renal cancer, and describe the histiogenesis and prognosis of renal cancer.

S22 was not detected on any normal fetal or adult tissues but was found on a subset of renal cancers. S4, F23, S23, and S27 defined distinct domains of the nephron: glomerulus (S4), proximal tubules (S4, F23, S23, S27), and portions of Henle's loop (S23 and S27). mAbS4 also reacted with the interstitial matrix in the renal medulla and of other tissues, and mAbF23 reacted with fetal and adult fibroblasts. The S23 epitope of ADA-BP was expressed by placental trophoblasts and epithelial cells of breast, prostate, lung, and colon, whereas the S27 epitope was detected on a more limited range of cell types (trophoblasts and prostate epithelium). A panel of 20 renal cell carcinomas was typed for expression of these antigens; 7 phenotypes could be distinguished, with the S4+/F23+/S23+/S27+/S22+ or − phenotype (15 cases) being most common. The other antigenic system, V1, identified a heat-stable antigen that was widely expressed on cultured cell types but showed a restricted pattern of reactivity in tissues. V1 expression was limited to the adrenal cortex, Leydig cells, and the theca of ovarian follicles, and to adrenal cortical carcinomas.

In a further study of mAb several more were discovered which react to serve to phenotype renal cell carinoma though the mAbs were not originally derived from renal cell immunogen. C26 is derived from gastrointestinal immunogen, J143 and T16 from bladder immunogen, AJ8 from astrocytoma immunogen and Q14 from melanoma immunogen (See Table IV). Table V shows localization of cell surface antigens on the normal adult nephron with mAb. Table VI and VII summarize tissue reactivity of mAb S4, F23, S23, S27, S22, V1, Q14, J143, AJ8, C26, T16.

Eight mouse monoclonal antibodies (mAb) defining cell surface antigens (Ag) of cultured human renal cancer were tested for reactivity with normal and neoplastic tissues. Each mAb identified distinct glycoproteins with $M_r 160,000$ (S4); $M_r 100,000$ (AJ8); $M_r 140,000$ (F23); $M_r 120,000$ (S23, S27); $M_r 40,000$ (C26); $M_r 48,000/42,000$ (T16) and $M_r 115,000$ (S22). S22 was not detected on normal fetal or adult tissues but was found on some renal cancers. Other mAbs defined distinct domains of adult nephron glomerulus (S4, AJ8), proximal tubule (S4, AJ8, F23, S23, S27), portions of Henle's loop (S23, S27, C26, T16) and distal tubule, collecting duct, urothelium (C26, T16). mAbS4 also reacted with interstitial matrix and vessels and mAbF23 reacted with fibroblasts. mAbS23, mAbS27 defined distinct epitopes on adenosine deaminase binding protein [J Biol Chem 259:12844 (1984)]; binding protein was also found on trophoblasts and epithelial cells of breast, prostate, lung and colon. Fetal kidney was analyzed for Ag expression during metanephric development. C26 was detected on blastema cells after induction and T16 was found on ureter bud. Distinct proximal tubule Ags were initially expressed at different stages of nephron development. (See Table V) Primary and metastatic renal tumors were also typed for Ag expression Several phenotypes were found for renal cell carcinoma. S4+/AJ8−/F23+/S23+/S27+/C26−/T16−/S2-2+or − phenotype was most common. Table VIII shows their reaction with human kidney (fetal); Table IX A & B with human tumors.

AJ8 is disclosed in a publication Cairncross et al. (1982) Proc. Nat'l. Acad. Sci. U.S.A. 79: 5641 and a copending patent application Ser. No. 413,861 both hereby incorporated by reference.

The following hybridoma lines and maintained on deposit at Sloan-Kettering Institute for Cancer Research, 1275 York Avenue, New York, N.Y. 10021 under designations corresponding to the mAb produced by each hybridoma as follows $S_4$, $S_{22}$, $S_{23}$, $S_{27}$, $F_{23}$, $V_1$, T16, C26, AJ8, J143, Q14, J143, AJ8, C26, T16, F31, T110, T138, T45, and Om5.

Hybridoma lines have been deposited with the American Type Culture Collection (ATCC) 12301 Parklawn Drive, Rockville, Md. 20852 under ATCC designations corresponding to the above Sloan-Kettering designations and alternate designations in parenthesis, as follows:

| mAb | Deposit date | Corresponding ATCC Accession No. |
|---|---|---|
| S4 (URO2) | April 17, 1984 | HB 8541 |
| S22 (URO7) | April 17, 1984 | HB 8542 |
| S23 | April 17, 1984 | HB 8540 |
| S27 (URO4) | November 15, 1983 | HB 8428 |
| V1 | November 15, 1983 | HB 8424 |
| F23 (URO3) | March 11, 1983 | HB 8231 |
| Q14 | | |
| J143 (URO1) | March 11, 1983 | HB 8276 |
| AJ8 | August 16, 1983 | HB 8339 |
| C26 (HT 29/26) | March 11, 1983 | HB 8247 |

| mAb | Deposit date | Corresponding ATCC Accession No. | mAb | Deposit date | Corresponding ATCC Accession No. |
|---|---|---|---|---|---|
| T16 (URO 5) | March 11, 1983 | HB 8279 | T138 (EC1) | March 11, 1983 | HB 8277 |
| F31 (URO8) | April 23, 1984 | HB 8548 | T43 (URO10) | March 11, 1983 | HB 8275 |
| T110 (URO6) | March 11, 1983 | HB 8278 | Om5 (URO9) | March 11, 1983 | HB 8270 |

TABLE IA

SEROLOGICAL REACTION OF mAbs PRODUCED FROM HUMAN RENAL TUMORS AND NORMAL EPITHELIUM AS IMMUNOGEN WITH VARIOUS CANCER CELL LINES AND NORMAL CELL LINES

| | *S4 | *S25 | *S22 | *S23 | *S6 | *S27 | *V1 | *S21 | F23 | M2 | S8 |
|---|---|---|---|---|---|---|---|---|---|---|---|
| Ig class of antibody: | γ2a | γ1 | γ1 | γ1 | γ1 | γ1 | γ1 | γ1 | γ2a | μ | μ |
| Antigen detected: | gp160 | | gp115 | gp120r | gp120nr | gp120nr | | gp45 β2 | gp140 | | |
| CELLS TESTED | | | | | | | | | | | |
| Renal Cell Lines | | | | | | | | | | | |
| *SK-RC-1 | 3 | 1 | 1 | 2 | 3 | 3 | 3 | 3 | | | |
| *SK-RC-2 | 0 | 0 | 1 | 0 | 3 | 3 | 3 | 3 | | | |
| *SK-RC-4 | 3 | 3 | 3 | 3 | 3 | 3 | 3 | 3 | 0 | 0 | 2 |
| *SK-RC-6 | 3 | 0 | 2 | 3 | 3 | 3 | 3 | 3 | | | |
| *SK-RC-7 | 3 | 3 | 3 | 2 | 3 | 3 | 3 | 3 | 1 | 0 | 2 |
| *SK-RC-8 | 0 | 2 | 3 | 2 | 3 | 3 | 3 | 3 | | | |
| *SK-RC-9 | 0 | 1 | 3 | 1 | 3 | 3 | 3 | 3 | | | |
| *SK-RC-11 | 2 | 1 | 1 | 2 | 3 | 3 | 3 | 3 | | | |
| SK-RC-12 | 3 | | 0 | 2 | | 3 | | | 0 | | |
| SK-RC-13 | 3 | | 0 | 2 | | 3 | | | 0 | | |
| SK-RC-15 | 3 | | 0 | 3 | | 3 | | | 0 | | |
| SK-RC-16 | 2 | | 0 | 1 | | 3 | | | 0 | | |
| SK-RC-17 | 0 | | 0 | 0 | | 3 | | | 2 | | |
| SK-RC-18 | 2 | | 0 | 0 | | 3 | | | 2 | | |
| SK-RC-20 | 1 | | 0 | 1 | | 3 | | | 1 | | |
| *SK-RC-21 | 0 | 0 | 1 | 0 | 3 | 3 | 2 | 3 | 1 | | |
| SK-RC-24 | 3 | | 0 | 2 | | 3 | | | 3 | | |
| SK-RC-26a | 2 | | 1 | 1 | | 3 | | | 0 | | |
| SK-RC-26b | 3 | | 0 | 1 | | 3 | | | 0 | | |
| *SK-RC-28 | 3 | 1 | 1 | 3 | 3 | 3 | 3 | 3 | | 2 | 0 |
| *SK-RC-29 | 0 | 0 | 1 | 0 | 3 | 3 | 3 | 3 | | | |
| SK-RC-33 | 2 | | 2 | 2 | | 3 | | | 3 | | |
| SK-RC-34 | 3 | | 3 | 3 | | 3 | | | 2 | | |
| SK-RC-35 | 3 | | 3 | 3 | | 3 | | | 3 | | |

| | ANTIBODY | | | | | | | | | | |
|---|---|---|---|---|---|---|---|---|---|---|---|
| | *S4 | *S25 | *S22 | *S23 | *S6 | *S27 | *V1 | *S21 | F23 | M2 | S8 |
| CELLS TESTED | | | | | | | | | | | |
| Renal Cell Lines | | | | | | | | | | | |
| SK-RC-37 | 1 | | 0 | 1 | | 3 | | | 2 | | |
| SK-RC-38 | 3 | | 0 | 3 | | 3 | | | 2 | | |
| SK-RC-39 | 3 | | 1 | 3 | | 3 | | | 3 | | |
| SK-RC-40 | 3 | | 2 | 3 | | 3 | | | 3 | | |
| SK-RC-41 | 2 | | 0 | 3 | | 3 | | | 2 | | |
| SK-RC-42 | 0 | | 0 | 0 | | 3 | | | 2 | | |
| SK-RC-44 | 3 | | 1 | 2 | | 3 | | | 1 | | |
| SK-RC-45 | 3 | | 0 | 3 | | 3 | | | 3 | | |
| SK-RC-46 | 3 | | 0 | 0 | | 3 | | | 0 | | |
| A-498 | 3 | 0 | 1 | 1 | 3 | 3 | 3 | 3 | | | |
| CaKi-1 | 0 | 0 | 1 | 0 | 3 | 3 | 3 | 3 | | | |
| Normal kidney epithelium | | | | | | | | | | | |
| NK-LI | 3 | | 2 | 2 | | 3 | | | 2 | | |
| NK-LD | 2 | | 0 | 1 | | 3 | | | 1 | | |
| *NK-ID | | 0 | 2 | 0 | 2 | 2 | 2 | 3 | | | |
| *NK-EQ | 3 | 0 | 2 | 0 | 2 | 2 | 2 | 3 | | | |
| *NK-HY | 3 | 0 | 2 | 0 | 2 | 2 | 2 | 3 | | | |
| *NK-GM | 2 | 2 | 2 | 0 | 2 | 2 | 2 | 3 | | | |
| *NK-FR | 2 | 2 | 2 | 0 | 2 | 2 | 2 | 3 | | | |
| *NK-EI | 2 | 1 | 2 | 0 | 2 | 2 | 2 | 3 | | | |
| *NK-IJ | 2 | 1 | 2 | 0 | 2 | 2 | 2 | 3 | | | |
| *NK-EG | 2 | 0 | 2 | 0 | 2 | 2 | 2 | 3 | | | |
| *NK-GR | 2 | 0 | 2 | 0 | 2 | 2 | 2 | 3 | | | |
| *NK-IB | 2 | 0 | 2 | 0 | 2 | 2 | 2 | 3 | | 0 | 2 |
| Normal fetal kidney cells | | | | | | | | | | | |
| *FK-C4 | 2 | 2 | 2 | 0 | 2 | 2 | 2 | 3 | | | |
| *FK-C6 | 0 | 2 | 2 | 0 | 2 | 2 | 2 | 3 | | | |
| *FK-C8 | 2 | 2 | 2 | 0 | 2 | 2 | 2 | 3 | | | |
| Epithelial cancer cell lines | | | | | | | | | | | |
| Bladder cell lines | | | | | | | | | | | |

TABLE IA-continued
SEROLOGICAL REACTION OF mAbs PRODUCED FROM HUMAN RENAL TUMORS AND NORMAL EPITHELIUM AS IMMUNOGEN WITH VARIOUS CANCER CELL LINES AND NORMAL CELL LINES

| | | | | | | | | | | | |
|---|---|---|---|---|---|---|---|---|---|---|---|
| *RT-4 | 0 | 0 | 1 | 0 | 0 | 0 | 3 | 3 | | | |
| *5637 | 0 | 0 | 1 | 0 | 0 | 0 | 0 | 3 | | | |
| *T-24 | 0 | 0 | 1 | 0 | 2 | 2 | 0 | 3 | | | |
| *253J | 0 | 0 | 1 | 0 | 2 | 2 | 3 | 3 | | 2 | 0 |
| Breast cell lines | | | | | | | | | | | |
| *AlAb | 0 | 0 | 0 | 0 | 0 | 0 | 2 | 3 | | | |
| *BT-20 | 0 | 0 | 0 | 0 | 0 | 0 | 0 | 3 | | | |
| *MCF-7 | 0 | 0 | 0 | 0 | 0 | 0 | 3 | 3 | | | |
| *SK-BR-3 | 0 | 0 | 0 | 0 | 0 | 0 | 3 | 3 | | 0 | 2 |
| Cervix cell line | | | | | | | | | | | |
| *ME-180 | 0 | 0 | 0 | 0 | 0 | 0 | 1 | 1 | | 2 | 0 |
| Colon cell lines | | | | | | | | | | | |
| *HT-29 | 0 | 0 | 0 | 0 | 2 | 2 | 1 | 3 | | 2 | 0 |
| *SW-1222 | 0 | 0 | 0 | 0 | 0 | 0 | 3 | 2 | | 2 | 0 |
| Lung cell lines | | | | | | | | | | | |
| *SK-LC-LL | 0 | 0 | 1 | 0 | 0 | 0 | 2 | 2 | | | |
| *SK-LC-6 | 0 | 0 | 0 | 0 | 3 | 3 | 3 | 3 | | | |
| Ovary cell line | | | | | | | | | | | |
| *SK-OV-3 | 0 | 0 | 2 | 0 | 0 | 0 | 1 | 3 | | | |
| Normal cell lines | | | | | | | | | | | |
| *Adult skin fibroblast | 0 | 0 | 0 | 0 | 2 | 2 | 0 | 2 | | | |
| *Fetal lung fibroblast | 0 | 0 | 2 | 0 | 2 | 2 | 2 | 3 | 3 | | |
| Neuroectoderm cancer cell lines | | | | | | | | | | | |
| Astrocytoma | | | | | | | | | | | |
| *SK-MG-1 | 0 | 0 | 1 | 0 | 0 | 0 | 0 | 3 | | | |
| *SK-MG-4 | 0 | 0 | 1 | 0 | 0 | 0 | 0 | 3 | | | |
| *SK-MG-7 | 0 | 0 | 1 | 0 | 0 | 0 | 0 | 3 | | | |
| Melanoma | | | | | | | | | | | |
| *SK-MEL-13 | 0 | 0 | 0 | 0 | 0 | 0 | 3 | 3 | | | |
| *SK-MEL-19 | 0 | 0 | 0 | 0 | 0 | 0 | 3 | 1 | | | |
| *SK-MEL-28 | 0 | 0 | 0 | 0 | 0 | 0 | 3 | 3 | | | |
| *SK-MEL-29 | 0 | 0 | 0 | 0 | 0 | 0 | 3 | 3 | | | |
| *SK-MEL-37 | 0 | 0 | 0 | 0 | 0 | 0 | 3 | 3 | | | |
| *SK-MEL-41 | 0 | 0 | 0 | 0 | 0 | 0 | 3 | 3 | | | |
| Neuroblastoma | | | | | | | | | | | |
| *SK-NMC | 0 | 0 | 0 | 0 | 0 | 0 | 2 | 3 | | | |
| *SK-NSH | 0 | 0 | 0 | 0 | 0 | 0 | 2 | 3 | | | |
| Normal primary cultures | | | | | | | | | | | |
| *Fetal brain | 0 | 0 | 5 | 0 | 4 | 4 | 4 | 3 | | | |
| #Fetal melanocytes | 0 | 0 | 0 | 3 | 3 | | 3 | 3 | | | |
| #Adult melanocytes | 0 | 0 | 0 | 3 | 3 | | 3 | 3 | | | |
| Hematopoetic cancer cell lines | | | | | | | | | | | |
| Lymphoblastoid cells | | | | | | | | | | | |
| *EBV B cells -AX | 4 | 4 | 4 | 4 | 4 | 4 | 5 | 5 | | | |
| *EBV B cells - BE | 4 | 4 | 4 | 4 | 4 | 4 | 5 | 5 | | | |
| *EBV B cells - EU | 4 | 4 | 4 | 4 | 4 | 4 | 5 | 5 | | | |
| *Burkitt's Lym - Daud. | 4 | 4 | 4 | 4 | 4 | 4 | 5 | 5 | | | |
| *Burkitt's Lym - Raji | 4 | 4 | 4 | 4 | 4 | 4 | 5 | 5 | | | |
| + Cells - Molt-4 | 4 | 4 | 4 | 4 | 4 | 4 | 4 | 5 | | | |
| *T cells - T-45 | 4 | 4 | 4 | 4 | 4 | 4 | 4 | 5 | | | |
| Normal cells | | | | | | | | | | | |
| *Erythrocytes - A | 4 | 4 | 4 | 4 | 4 | 4 | 4 | 4 | 4 | 3 | 0 |
| *Erythrocytes - B | 4 | 4 | 4 | 4 | 4 | 4 | 4 | 4 | 4 | 0 | 3 |
| *Erythrocytes - O | 4 | 4 | 4 | 4 | 4 | 4 | 4 | 4 | 4 | 0 | 0 |
| Xenogeneic cells | | | | | | | | | | | |
| *Monkey kidney - VERO | 0 | 0 | 0 | 0 | 3 | 0 | 0 | 0 | | | |
| *Sheep erythrocytes | 4 | 4 | 4 | 4 | 4 | 4 | 4 | 4 | | 0 | 0 |

References
*Ueda, R., Ogata, S.-I., Morrissey, D. M., Finstad, C. L., Szkudlarek, J., Whitmore, W. F., Oettgen, H. F., Lloyd, K. O. and Old, L. J. Cell surface antigens of human renal cancer defined by mouse monoclonal antibodies: Identification of tissue specific kidney glycoproteins. Proc. Nat. Acad. Sci. 78:5122-5126 (1981).
Houghton, A. N., Eisinger, M. Albino, A. P., Cairncross, J. G. and Old, L. J. Surface antigens of melanocytes and melanomas. Markers of melanocyte differentiation and melanoma subsets.
Legend to Table IA
Serological Reaction of monoclonal antibodies of Ueda et al supra (*) and F23 mAb with tumor cell lines and normal cell lines.
0 = no reaction either by absorption or rosette formation
1 = reaction by absorption only
2 = reaction by rosette formation titer less than 10,000
3 = reaction by rosette formation titer greater than 10,000
4 = no reaction - only absorption test done
5 = reaction with absorption test only

TABLE IB

Serological characterization of seven prototype mouse Abs detecting surface antigens on human renal cancer cells

| Cells | Ab S$_4$ Titer × 10$^{-3}$ | Abs. | Ab S$_{25}$ Titer × 10$^{-3}$ | Abs. | Ab S$_{23}$ Titer × 10$^{-3}$ | Abs. | Ab S$_6$ Titer × 10$^{-3}$ | Abs. | Ab S$_{22}$ Titer × 10$^{-3}$ | Abs. | Ab V$_1$ Titer × 10$^{-3}$ | Abs. | Ab S$_{21}$ Titer × 10$^{-3}$ | Abs. |
|---|---|---|---|---|---|---|---|---|---|---|---|---|---|---|
| Epithelial cancers | | | | | | | | | | | | | | |
| Renal | | | | | | | | | | | | | | |
| SK-RC-1(AA) | 50 | + | — | + | 1 | + | 50 | + | — | + | 500 | + | 50000 | + |
| SK-RC-2(AB) | — | — | — | — | — | — | 50 | + | — | + | 500 | + | 5000 | + |
| SK-RC-4(AE) | 50 | + | 500 | + | 50 | + | 50 | + | 5000 | + | 10000 | + | 5000 | + |
| SK-RC-6(AG) | 50 | + | — | — | 10 | + | 1000 | + | 5 | + | 10000 | + | 100000 | + |
| SK-RC-7(AX) | 50 | + | 500 | + | 1 | + | 500 | + | 10000 | + | 10000 | + | 50000 | + |
| SK-RC-8(BE) | — | — | 1 | + | 1 | + | 50 | + | 50 | + | 50 | + | 500 | + |
| SK-RC-9(BM) | — | — | — | + | — | + | 500 | + | 50 | 5000 | + | 50000 | + | |
| SK-RC-11(BZ) | 5 | + | — | + | 1 | + | 1000 | + | — | + | 10000 | + | 50000 | + |
| SK-RC-21(EB) | — | — | — | — | — | — | 500 | + | — | + | 1 | + | 50000 | + |
| SK-RC-28(EU) | 50 | + | — | + | 500 | + | 5000 | + | — | + | 500 | + | 100000 | + |
| SK-RC-29(BW) | 10 | + | — | — | — | + | 50 | + | — | + | 10000 | + | 100 | + |
| A-498 | 10 | + | — | — | — | + | 50 | + | — | + | 10000 | + | 100 | + |
| CaKi-1 | — | — | — | — | — | — | 50 | + | — | + | 10000 | + | 100 | + |
| Bladder | | | | | | | | | | | | | | |
| RT-4 | — | — | — | — | — | — | — | — | — | + | 5000 | + | 50 | + |
| 5637 | — | — | — | — | — | — | — | — | — | + | — | — | 10 | + |
| T-24 | — | — | — | — | — | — | 5 | + | — | + | — | — | 10000 | + |
| 253J | — | — | — | — | — | — | 5 | + | — | + | 5000 | + | 5000 | + |
| Breast | | | | | | | | | | | | | | |
| AlAb | — | — | — | — | — | — | — | — | — | — | 5 | + | 500 | + |
| BT-20 | — | — | — | — | — | — | — | — | — | — | — | — | 50 | + |
| MCF-7 | — | — | — | — | — | — | — | — | — | — | 10000 | + | 1000 | + |
| SK-BR-3 | — | — | — | — | — | — | — | — | — | — | 10000 | + | 10 | + |
| Cervix | | | | | | | | | | | | | | |
| ME-180 | — | — | — | — | — | — | — | — | — | — | — | + | — | + |
| Colon | | | | | | | | | | | | | | |
| HT-29 | — | — | — | — | — | — | 5 | + | — | — | — | + | 50 | + |
| SW-1222 | — | — | — | — | — | — | — | — | — | — | 500 | + | 5 | + |
| Lung | | | | | | | | | | | | | | |
| SK-LC-LL | — | — | — | — | — | — | — | — | — | + | 1 | + | 5 | + |
| SK-LC-6 | — | — | — | — | — | — | 50 | + | — | — | 10000 | + | 50000 | + |
| Ovary | | | | | | | | | | | | | | |
| SK-OV-3 | — | — | — | — | — | — | — | — | 0.5 | + | — | + | 50 | + |
| Testicular | | | | | | | | | | | | | | |
| SK-GR-1 | — | — | — | — | — | — | — | — | — | — | — | + | 1 | + |
| Astrocytomas: | | | | | | | | | | | | | | |
| AJ,AS,BE | — | — | — | — | — | — | 5 | + | — | + | — | — | 500 | + |
| Melanomas: | | | | | | | | | | | | | | |
| SK-MEL-13,28,29,37,41 | — | — | — | — | — | — | — | — | — | — | 5000 | + | 5000 | + |
| SK-MEL-19 | — | — | — | — | — | — | — | — | — | — | 5000 | + | — | + |
| Neuroblastomas: | | | | | | | | | | | | | | |
| SK-NMC,SK-NSH | — | — | — | — | — | — | — | — | — | — | 1 | + | 100 | + |
| Lymphoblastoid cells: | | | | | | | | | | | | | | |
| EBV B cells AX,BE,EU | | | — | — | — | — | — | — | — | — | | + | | + |
| Burkitt's lymphomas Raji, Daudi | | | — | — | — | — | — | — | — | — | | + | | + |
| T cells MOLT-4,T-45 | | | — | — | — | — | — | — | — | — | | — | | + |
| Normal human cells: | | | | | | | | | | | | | | |
| Kidney epithelium | | | | | | | | | | | | | | |
| ID | | | — | — | 10 | + | 5 | + | 1 | + | 5 | + | 25 | + |
| EQ,HY | 10 | + | — | — | 1.5 | + | 5 | + | 1 | + | 5 | + | 25 | + |
| GM,FR | 3 | + | 3 | + | 3 | + | 5 | + | 1 | + | 5 | + | 25 | + |
| EI,IJ | 3 | + | — | + | 1.5 | + | 5 | + | 1 | + | 5 | + | 25 | + |
| EG,GR,IB | 0.5 | + | — | — | 0.5 | + | 5 | + | 1 | + | 5 | + | 25 | + |
| Fetal kidney | | | | | | | | | | | | | | |
| C-4,C-8 | 0.5 | + | 2 | + | — | — | >5 | + | >5 | + | >5 | + | >5 | + |
| C-6 | — | — | 2 | + | — | — | >5 | + | >5 | + | >5 | + | >5 | + |
| Adult skin fibroblasts | — | — | — | — | — | — | 5 | + | — | — | — | — | 5 | + |
| Fetal lung fibroblasts | — | — | — | — | — | — | 1.5 | + | 0.5 | + | 0.5 | + | 10 | + |
| Fetal brain | — | — | — | — | — | — | — | — | — | + | — | — | 10 | + |
| Erythrocytes | — | — | — | — | — | — | — | — | — | — | — | — | — | — |
| Xenogeneic cells: | | | | | | | | | | | | | | |
| Monkey kidney VERO | — | — | — | — | — | — | 5 | + | — | — | — | — | — | — |

TABLE IB-continued

Serological characterization of seven prototype mouse Abs detecting surface antigens on human renal cancer cells

| Cells | Ab S4 Titer × $10^{-3}$ | Abs. | Ab S25 Titer × $10^{-3}$ | Abs. | Ab S23 Titer × $10^{-3}$ | Abs. | Ab S6 Titer × $10^{-3}$ | Abs. | Ab S22 Titer × $10^{-3}$ | Abs. | Ab V1 Titer × $10^{-3}$ | Abs. | Ab S21 Titer × $10^{-3}$ | Abs. |
|---|---|---|---|---|---|---|---|---|---|---|---|---|---|---|
| Sheep erythrocytes | — | | — | | — | | — | | — | | — | | — | |

Under "Titer"- indicates no reaction in direct tests at a dilution of 1:200. Abs., absorption tests. Sera (diluted to end point) were absorbed with the indicated cell type and tested for residual activity for SK-RC-7 (Ab S4, Ab S6, Ab S22, Ab S21), SK-RC-4 (Ab S25), SK-RC-6 (Ab V1), or SK-RC-28 (Ab S23) target cells; +, complete absorption; -, no absorption. *mAb S27 is derived from SK-RC-7 and has essentially the reactivity of mAb S6.

TISSUE DISTRIBUTION OF THE MONOCLONAL ANTIBODIES OF THE KIDNEY

A. FETAL TISSUES (NORMAL)

|  | S4 | S6/S7 | S23 | F23 | S22 | Q14 | AJ8 | NL-1 | NL-22 | P170 140 | C26 | C68 |
|---|---|---|---|---|---|---|---|---|---|---|---|---|
| LUNG | 0 | 0 | 0 | 0 | 0 | 0 | 0 | 0 | 0 | 0 | + | 0 |
| Bronchial Epithelium | 0 | 0 | 0 | 0 | 0 | 0 | 0 | 0 | 0 | 0 | + | 0 |
| Cartilage | 0 | 0 | 0 | 0 | 0 | 0 | 0 | 0 | 0 | 0 | 0 | 0 |
| Pneumocytes | 0 | 0 | 0 | 0 | 0 | 0 | 0 | 0 | 0 | 0 | 0 | 0 |
| Connect. Tis | 0 | 0 | 0 | 0 | 0 | 0 | 0 | 0 | 0 | 0 | 0 | 0 |
| HEART | 0 | 0 | 0 | 0 | 0 | 0 | 0 | 0 | 0 | 0 | 0 | 0 |
| THYMUS | 0 | 0 | 0 | 0 | 0 | 0 | 0 | 0 | 0 | 0 | 0 | + |
| Hassal's C. | 0 | 0 | 0 | 0 | 0 | 0 | 0 | 0 | 0 | 0 | 0 | + |
| Thymocytes | 0 | 0 | 0 | 0 | 0 | 0 | 0 | 0 | 0 | 0 | 0 | 0 |
| SPLEEN | 0 | 0 | 0 | 0 | 0 | 0 | 0 | 0 | 0 | 0 | 0 | 0 |
| White Pulp | 0 | 0 | 0 | 0 | 0 | 0 | 0 | 0 | 0 | 0 | 0 | 0 |
| Red Pulp | 0 | 0 | 0 | 0 | 0 | 0 | 0 | 0 | 0 | 0 | 0 | 0 |
| LIVER | 0 | 0 | 0 | 0 | 0 | 0 | 0 | 0 | 0 | 0 | + | + |
| Hepatocytes | 0 | 0 | 0 | 0 | 0 | 0 | 0 | 0 | 0 | 0 | 0 | 0 |
| Biliary Epi. Cells | 0 | 0 | 0 | 0 | 0 | 0 | 0 | 0 | 0 | 0 | + | + |
| GALLBLAD. | 0 | 0 | 0 | 0 | 0 | 0 | 0 | 0 | 0 | 0 | + | + |
| ESOPHAGUS | 0 | 0 | 0 | 0 | 0 | 0 | 0 | 0 | 0 | 0 | ± | ± |
| STOMACH | 0 | 0 | 0 | 0 | 0 | 0 | 0 | 0 | 0 | 0 | 0 | + |
| SMALL INT. | 0 | 0 | 0 | 0 | 0 | 0 | 0 | 0 | 0 | 0 | ± | + |
| COLON | 0 | 0 | 0 | 0 | 0 | 0 | 0 | 0 | 0 | 0 | + | + |
| PANCREAS | 0 | 0 | 0 | 0 | 0 | 0 | 0 | 0 | 0 | 0 | + | 0 |
| Exocrine | 0 | 0 | 0 | 0 | 0 | 0 | 0 | 0 | 0 | 0 | + | 0 |
| Endocrine | 0 | 0 | 0 | 0 | 0 | 0 | 0 | 0 | 0 | 0 | 0 | 0 |
| KIDNEY | + | + | + | + | 0 | + | + | + | 0 | + | + | 0 |
| Glomerulus | + | 0 | 0 | 0 | 0 | + | + | + | 0 | + | 0 | 0 |
| Prox. Tub. | + | + | + | + | 0 | 0 | + | + | 0 | 0 | 0 | 0 |
| Distal Tub. | 0 | 0 | 0 | 0 | 0 | 0 | 0 | 0 | 0 | 0 | + | 0 |
| Collec. Tub. | 0 | 0 | 0 | 0 | 0 | 0 | 0 | 0 | 0 | 0 | + | 0 |
| URETER | 0 | + | 0 | 0 | 0 | 0 | 0 | 0 | 0 | 0 | + | + |
| UR. BLAD. | 0 | + | 0 | 0 | 0 | 0 | 0 | 0 | 0 | 0 | + | + |
| ADRENAL | 0 | 0 | 0 | 0 | 0 | 0 | 0 | 0 | 0 | 0 | 0 | 0 |
| Cortex | 0 | 0 | 0 | 0 | 0 | 0 | 0 | 0 | 0 | 0 | 0 | 0 |
| Medulla | 0 | 0 | 0 | 0 | 0 | 0 | 0 | 0 | 0 | 0 | 0 | 0 |
| TESTES | 0 | 0 | 0 | 0 | 0 | 0 | 0 | 0 | 0 | 0 | 0 | 0 |
| Germ. Cells | 0 | 0 | 0 | 0 | 0 | 0 | 0 | 0 | 0 | 0 | 0 | 0 |
| Endoc. Cel. | 0 | 0 | 0 | 0 | 0 | 0 | 0 | 0 | 0 | 0 | 0 | 0 |
| Connect. T. | 0 | 0 | 0 | 0 | 0 | 0 | 0 | 0 | 0 | 0 | 0 | 0 |
| OVARY | 0 | 0 | 0 | 0 | 0 | 0 | 0 | 0 | 0 | 0 | 0 | 0 |
| Germ. Cells | 0 | 0 | 0 | 0 | 0 | 0 | 0 | 0 | 0 | 0 | 0 | 0 |
| Connect. T. | 0 | 0 | 0 | 0 | 0 | 0 | 0 | 0 | 0 | 0 | 0 | 0 |
| FALLOP. T. | 0 | 0 | 0 | 0 | 0 | 0 | 0 | 0 | 0 | 0 | + | 0 |
| UTERUS | 0 | 0 | 0 | 0 | 0 | 0 | 0 | 0 | 0 | 0 | + | 0 |
| Endometrium | 0 | 0 | 0 | 0 | 0 | 0 | 0 | 0 | 0 | 0 | + | 0 |
| Myometrium | + | 0 | 0 | 0 | 0 | 0 | 0 | 0 | 0 | 0 | 0 | 0 |
| CERVIX | 0 | 0 | 0 | 0 | 0 | 0 | 0 | 0 | 0 | 0 | + | + |
| Endocervix | 0 | 0 | 0 | 0 | 0 | 0 | 0 | 0 | 0 | 0 | + | 0 |
| Exocervix | 0 | 0 | 0 | 0 | 0 | 0 | 0 | 0 | 0 | 0 | 0 | + |
| SKIN | 0 | 0 | 0 | 0 | 0 | 0 | 0 | 0 | 0 | 0 | + | + |
| Epidermis | 0 | 0 | 0 | 0 | 0 | 0 | 0 | 0 | 0 | 0 | ± | ± |
| Melanocytes | 0 | 0 | 0 | 0 | 0 | 0 | 0 | 0 | 0 | 0 | 0 | 0 |
| Sweat Gland | 0 | 0 | 0 | 0 | 0 | 0 | 0 | 0 | 0 | 0 | + | 0 |
| Sebac. Gld. | 0 | 0 | 0 | 0 | 0 | 0 | 0 | 0 | 0 | 0 | 0 | 0 |
| Hair Fol. | 0 | 0 | 0 | 0 | 0 | 0 | 0 | 0 | 0 | 0 | 0 | 0 |
| Dermis C.T. | 0 | 0 | 0 | 0 | 0 | 0 | 0 | 0 | 0 | 0 | 0 | 0 |
| BRAIN | 0 | 0 | 0 | 0 | 0 | 0 | 0 | 0 | 0 | 0 | 0 | 0 |
| Neurons | 0 | 0 | 0 | 0 | 0 | 0 | 0 | 0 | 0 | 0 | 0 | 0 |
| Glial Cells | 0 | 0 | 0 | 0 | 0 | 0 | 0 | 0 | 0 | 0 | 0 | 0 |
| Dendrites | 0 | 0 | 0 | 0 | 0 | 0 | 0 | 0 | 0 | 0 | 0 | 0 |
| LYMPH NODE | 0 | 0 | 0 | 0 | 0 | 0 | 0 | 0 | 0 | 0 | 0 | 0 |
| BLOOD VES. | + | 0 | 0 | 0 | 0 | + | 0 | 0 | 0 | 0 | 0 | 0 |
| Endoth. Cel. | 0 | 0 | 0 | 0 | 0 | + | 0 | 0 | 0 | 0 | 0 | 0 |

-continued

TISSUE DISTRIBUTION OF THE MONOCLONAL ANTIBODIES OF THE KIDNEY

| | | | | | | | | | | | | |
|---|---|---|---|---|---|---|---|---|---|---|---|---|
| Smooth Ms. | + | 0 | 0 | 0 | 0 | 0 | 0 | 0 | 0 | 0 | 0 | 0 |
| SOFT TIS. | 0 | 0 | 0 | 0 | 0 | 0 | + | 0 | 0 | + | 0 | 0 |
| SECRETION | 0 | 0 | 0 | 0 | 0 | 0 | 0 | 0 | 0 | 0 | + | + |

B. ADULT TISSUES (Normal)

| | S4 | S6/S7 | S23 | F23 | S22 | Q14 | AJ8 | NL-1 | NL-22 | P170 140 | C26 | C68 |
|---|---|---|---|---|---|---|---|---|---|---|---|---|
| LUNG | 0 | 0 | 0 | 0 | 0 | 0 | 0 | 0 | 0 | 0 | + | 0 |
| Bronchial Epithelium | 0 | 0 | 0 | 0 | 0 | 0 | 0 | 0 | 0 | 0 | + | 0 |
| Cartilage | 0 | 0 | 0 | 0 | 0 | 0 | 0 | 0 | 0 | 0 | 0 | 0 |
| Glandular Epithelium | 0 | 0 | 0 | 0 | 0 | 0 | 0 | 0 | 0 | 0 | + | 0 |
| Pneumocytes | 0 | 0 | 0 | 0 | 0 | 0 | 0 | 0 | 0 | 0 | 0 | 0 |
| Connect. Tis. | 0 | 0 | 0 | 0 | 0 | 0 | 0 | 0 | 0 | 0 | 0 | 0 |
| HEART (ms) | 0 | 0 | 0 | 0 | 0 | 0 | 0 | 0 | 0 | 0 | 0 | 0 |
| SPLEEN | 0 | 0 | 0 | 0 | 0 | 0 | 0 | 0 | 0 | 0 | 0 | 0 |
| White pulp | 0 | 0 | 0 | 0 | 0 | 0 | 0 | 0 | 0 | 0 | 0 | 0 |
| Red pulp | 0 | 0 | 0 | 0 | 0 | 0 | 0 | 0 | 0 | 0 | 0 | 0 |
| LIVER | 0 | 0 | 0 | 0 | 0 | 0 | 0 | 0 | 0 | 0 | + | 0 |
| Hepatocyte | 0 | 0 | 0 | 0 | 0 | 0 | 0 | 0 | 0 | 0 | 0 | 0 |
| Bil. Epit. | 0 | 0 | 0 | 0 | 0 | 0 | 0 | 0 | 0 | 0 | + | 0 |
| Sinusoids | 0 | 0 | 0 | 0 | 0 | 0 | 0 | 0 | 0 | 0 | 0 | 0 |
| GALLBLADDER | 0 | 0 | 0 | 0 | 0 | 0 | 0 | 0 | 0 | 0 | + | 0 |
| ESOPHAGUS | 0 | 0 | 0 | 0 | 0 | 0 | 0 | 0 | 0 | 0 | 0 | 0 |
| STOMACH | 0 | 0 | 0 | 0 | 0 | 0 | 0 | 0 | 0 | 0 | 0 | + |
| SM. INTEST. | 0 | 0 | 0 | 0 | 0 | 0 | 0 | 0 | 0 | 0 | 0 | + |
| COLON | 0 | + | + | 0 | 0 | 0 | 0 | 0 | 0 | 0 | + | + |
| G.I. Smc | 0 | 0 | 0 | 0 | 0 | 0 | 0 | 0 | 0 | 0 | 0 | 0 |
| PANCREAS | 0 | 0 | 0 | 0 | 0 | 0 | 0 | 0 | 0 | 0 | + | 0 |
| Exocrine | 0 | 0 | 0 | 0 | 0 | 0 | 0 | 0 | 0 | 0 | + | 0 |
| Endocrine | 0 | 0 | 0 | 0 | 0 | 0 | 0 | 0 | 0 | 0 | 0 | 0 |
| KIDNEY | + | + | + | + | 0 | + | + | + | + | + | + | 0 |
| Glomerulus | + | 0 | 0 | 0 | 0 | + | + | + | 0 | + | 0 | 0 |
| Prox. Tub. | + | + | + | + | 0 | 0 | + | + | + | 0 | 0 | 0 |
| Henle's L. | 0 | ± | 0 | 0 | 0 | 0 | ± | 0 | 0 | 0 | ± | 0 |
| Distal Tub. | 0 | 0 | 0 | 0 | 0 | 0 | 0 | 0 | 0 | 0 | + | 0 |
| Collec. Tub. | 0 | 0 | 0 | 0 | 0 | 0 | 0 | 0 | 0 | 0 | + | 0 |
| URETER | 0 | + | 0 | 0 | 0 | 0 | 0 | 0 | 0 | 0 | + | + |
| URI. BLAD. | 0 | + | 0 | 0 | 0 | 0 | 0 | 0 | 0 | 0 | + | + |
| ADRENAL | 0 | 0 | 0 | 0 | 0 | 0 | 0 | 0 | 0 | 0 | 0 | 0 |
| Cortex | 0 | 0 | 0 | 0 | 0 | 0 | 0 | 0 | 0 | 0 | 0 | 0 |
| Medulla | 0 | 0 | 0 | 0 | 0 | 0 | 0 | 0 | 0 | 0 | 0 | 0 |
| THYROID | 0 | 0 | 0 | 0 | 0 | 0 | 0 | 0 | 0 | 0 | 0 | 0 |
| Epithelium | 0 | 0 | 0 | 0 | 0 | 0 | 0 | 0 | 0 | 0 | 0 | 0 |
| Colloid | 0 | 0 | 0 | 0 | 0 | 0 | 0 | 0 | 0 | 0 | 0 | 0 |
| BREAST | 0 | 0 | 0 | 0 | 0 | 0 | 0 | 0 | 0 | 0 | + | + |
| Duct Cells | 0 | 0 | 0 | 0 | 0 | 0 | 0 | 0 | 0 | 0 | + | + |
| Acinar Cel. | 0 | 0 | 0 | 0 | 0 | 0 | 0 | 0 | 0 | 0 | + | 0 |
| Connec. Tis. | 0 | 0 | 0 | 0 | 0 | 0 | 0 | 0 | 0 | 0 | 0 | 0 |
| PROSTATE | 0 | + | + | 0 | 0 | 0 | 0 | 0 | 0 | 0 | + | + |
| Epithelium | 0 | + | + | 0 | 0 | 0 | 0 | 0 | 0 | 0 | + | + |
| Stroma | 0 | 0 | 0 | 0 | 0 | 0 | 0 | 0 | 0 | 0 | 0 | 0 |
| TESTE | 0 | 0 | 0 | 0 | 0 | 0 | 0 | 0 | 0 | 0 | 0 | 0 |
| Germ Cells | 0 | 0 | 0 | 0 | 0 | 0 | 0 | 0 | 0 | 0 | 0 | 0 |
| Endocrine Cells | 0 | 0 | 0 | 0 | 0 | 0 | 0 | 0 | 0 | 0 | 0 | 0 |
| Connec. Tis. | 0 | 0 | 0 | 0 | 0 | 0 | 0 | 0 | 0 | 0 | 0 | 0 |
| FALLOP. TUB. | 0 | 0 | 0 | 0 | 0 | 0 | 0 | 0 | 0 | 0 | 0 | 0 |
| UTERUS | 0 | 0 | 0 | 0 | 0 | 0 | 0 | 0 | 0 | 0 | + | 0 |
| Endometrium | 0 | 0 | 0 | 0 | 0 | 0 | 0 | 0 | 0 | 0 | + | 0 |
| Myometrium | + | 0 | 0 | 0 | 0 | 0 | 0 | 0 | 0 | 0 | 0 | 0 |
| CERVIX | 0 | 0 | 0 | 0 | 0 | 0 | 0 | 0 | 0 | 0 | + | + |
| Endocervix | 0 | 0 | 0 | 0 | 0 | 0 | 0 | 0 | 0 | 0 | + | 0 |
| Exocervix | 0 | 0 | 0 | 0 | 0 | 0 | 0 | 0 | 0 | 0 | + | + |
| PLACENTA | 0 | 0 | 0 | 0 | 0 | 0 | 0 | 0 | 0 | 0 | 0 | 0 |
| Cytotrophb, | 0 | 0 | 0 | 0 | 0 | 0 | 0 | 0 | 0 | 0 | 0 | 0 |
| Syncytotrb. | 0 | 0 | 0 | 0 | 0 | 0 | 0 | 0 | 0 | 0 | 0 | 0 |
| Sinusoids | 0 | 0 | 0 | 0 | 0 | 0 | 0 | 0 | 0 | 0 | 0 | 0 |
| SKIN | 0 | 0 | 0 | 0 | 0 | 0 | 0 | 0 | 0 | 0 | + | 0 |
| Epidermis | 0 | 0 | 0 | 0 | 0 | 0 | 0 | 0 | 0 | 0 | + | 0 |
| Melancoytes | 0 | 0 | 0 | 0 | 0 | 0 | 0 | 0 | 0 | 0 | 0 | 0 |
| Sweat Gld. | 0 | 0 | 0 | 0 | 0 | 0 | 0 | 0 | 0 | 0 | + | 0 |
| Sebaceous G. | 0 | 0 | 0 | 0 | 0 | 0 | 0 | 0 | 0 | 0 | + | 0 |
| Dermis CT | 0 | 0 | 0 | 0 | 0 | 0 | 0 | 0 | 0 | 0 | 0 | 0 |
| BRAIN | 0 | 0 | 0 | 0 | 0 | 0 | + | 0 | 0 | + | 0 | 0 |
| Neurons | 0 | 0 | 0 | 0 | 0 | 0 | ± | 0 | 0 | ± | 0 | 0 |
| Glial Cell | 0 | 0 | 0 | 0 | 0 | 0 | 0 | 0 | 0 | 0 | 0 | 0 |
| Dendrites | 0 | 0 | 0 | 0 | 0 | 0 | 0 | 0 | 0 | 0 | 0 | 0 |
| LYMPH NODE | 0 | 0 | 0 | 0 | 0 | 0 | 0 | 0 | 0 | 0 | 0 | 0 |
| Fol/Nedul | 0 | 0 | 0 | 0 | 0 | 0 | 0 | 0 | 0 | 0 | 0 | 0 |

-continued

| TISSUE DISTRIBUTION OF THE MONOCLONAL ANTIBODIES OF THE KIDNEY | | | | | | | | | | | | |
|---|---|---|---|---|---|---|---|---|---|---|---|---|
| BLOOD VES. | + | 0 | 0 | 0 | 0 | + | 0 | 0 | 0 | 0 | 0 | 0 |
| Endothelium | 0 | 0 | 0 | 0 | 0 | + | 0 | 0 | 0 | 0 | + | + |
| Smooth Ms. | + | 0 | 0 | 0 | 0 | 0 | 0 | 0 | 0 | 0 | 0 | 0 |
| CAPILLARIES | 0 | 0 | 0 | 0 | 0 | + | 0 | 0 | 0 | 0 | 0 | 0 |
| SKELETAL MS | 0 | 0 | 0 | 0 | 0 | 0 | 0 | 0 | 0 | 0 | 0 | 0 |
| SOFT TISSUE | 0 | 0 | 0 | + | 0 | 0 | 0 | 0 | 0 | + | 0 | 0 |
| SECRETIONS | 0 | 0 | 0 | 0 | 0 | 0 | 0 | 0 | 0 | + | + | + |

C. RENAL CARCINOMAS

| | S6 | S4 | F23 | S23 | S22 | S25 | S27 | C26 | T43 | T16 | T87 |
|---|---|---|---|---|---|---|---|---|---|---|---|
| RC #3 | + | + | + | 0 | 0 | 0 | 0 | +· | 0 | 0 | |
| RC #5 | + | ± | ± | ± | 0 | 0 | ± | ± | ± | ± | |
| RC #6 | + | + | + | + | ± | 0 | 0 | ± | 0 | 0 | |
| RC #2 | + | + | ± | + | 0 | 0 | ± | 0 | 0 | ± | |
| RC #7 | + | + | ± | + | 0 | 0 | 0 | ± | 0 | 0 | |
| RC #9 | + | ± | 0 | + | 0 | 0 | 0 | 0 | 0 | 0 | |
| RC #10 | + | 0 | 0 | + | ± | 0 | + | 0 | + | + | |
| RC #11 | + | + | ± | 0 | ± | 0 | ± | 0 | 0 | 0 | |
| RC #12 | + | + | + | 0 | 0 | 0 | 0 | 0 | 0 | 0 | |
| RC #13 | + | + | + | 0 | 0 | 0 | 0 | 0 | 0 | 0 | |
| RC #22 | + | 0 | ± | 0 | 0 | 0 | ± | + | 0 | + | |
| RC #23 | + | + | + | + | 0 | 0 | 0 | + | 0 | 0 | |
| RC #14 | + | ± | 0 | 0 | 0 | 0 | 0 | 0 | 0 | 0 | |
| RC #16 | + | + | ± | ± | 0 | | | 0 | 0 | 0 | 0 |
| RC #19 | + | + | ± | + | 0 | | + | 0 | + | 0 | 0 |
| RC #18 | + | 0 | 0 | 0 | 0 | | | | 0 | + | + |
| RC #21 | + | + | ± | + | ± | | + | 0 | 0 | | |
| RC #15 | + | 0 | 0 | 0 | 0 | | 0 | ± | + | | |
| Billoti (NSUH) | + | 0 | 0 | ± | 0 | | + | 0 | ± | 0 | 0 |
| Pipet (NYU) | + | ± | ± | + | ± | | + | 0 | 0 | 0 | 0 |
| RC #17 | + | ± | ± | ± | ± | | + | ± | ± | ± | |
| RC #20 | + | ± | ± | + | ± | | + | 0 | | 0 | 0 |
| RC #24 | + | 0 | ± | ± | ± | | ± | 0 | | 0 | |
| RC #25 | 0 | 0 | 0 | 0 | 0 | | 0 | 0 | 0 | 0 | 0 |

D. Summary of tumor immunopathology staining using FITC-rabbit anti-mouse IgG

| | | Melan. N9 | S4 | S22 | F23 | S23 | S27 | S25 | V1 | C26 | T16 | AJ8 | NL-1 |
|---|---|---|---|---|---|---|---|---|---|---|---|---|---|
| Colon | 82-18240 | 0 | 0 | 0 | 0 | ± | 0 | + | 0 | + | 0 | 0 | 0 |
| | 83-153 | 0 | 0 | 0 | 0 | + | 0 | + | 0 | + | 0 | 0 | 0 |
| | 82-16115 | 0 | 0 | 0 | 0 | + | 0 | + | 0 | + | 0 | 0 | 0 |
| | 82-21302 | 0 | 0 | 0 | 0 | 0 | 0 | + | 0 | + | 0 | 0 | 0 |
| | invad.adenoca | 0 | 0 | 0 | 0 | 0 | 0 | + | 0 | + | 0 | 0 | 0 |
| Lung | 83-692 | 0 | 0 | 0 | 0 | 0 | 0 | + | 0 | + | 0 | 0 | 0 |
| | 83-2016 | 0 | 0 | 0 | + | ± | 0 | + | 0 | + | + | 0 | 0 |
| | 83-323 | 0 | 0 | 0 | 0 | 0 | 0 | + | 0 | 0 | 0 | 0 | 0 |
| | 83-337 | 0 | 0 | 0 | 0 | 0 | 0 | + | 0 | + | + | 0 | 0 |
| | Oat cell ca | 0 | 0 | 0 | 0 | 0 | 0 | + | 0 | + | 0 | 0 | 0 |
| Breast | fibroadenoma | 0 | 0 | 0 | ± | 0 | 0 | 0? | 0 | + | 0 | 0 | 0 |
| | 82-15096 | 0 | 0 | 0 | + | 0 | 0 | + | 0 | + | + | 0 | 0 |
| | 82-7783 | 0 | 0 | 0 | 0 | 0 | 0 | + | 0 | + | + | 0 | 0 |
| | 82-14627 | 0 | 0 | 0 | 0 | 0 | 0 | +? | 0 | + | + | 0 | 0 |
| | met to lym. n. | 0 | 0 | 0 | 0 | 0 | 0 | + | 0 | + | 0 | 0 | 0 |
| Bladder | papilloma | 0 | 0 | 0 | 0 | 0 | 0 | + | 0 | + | + | 0 | 0 |
| | Arnold/in situ | 0 | 0 | 0 | 0 | 0 | 0 | 0? | 0 | 0 | + | 0 | 0 |
| | Grant TCC | 0 | 0 | 0 | 0 | 0 | 0 | 0? | 0 | 0 | + | 0 | 0 |
| | Wilson TCC | 0 | 0 | 0 | 0 | 0 | 0 | +? | 0 | + | + | 0 | 0 |
| | Caurin TCC | 0 | 0 | ± | 0 | 0 | 0 | + | 0 | + | + | 0 | 0 |
| Ureter | 82-20793 | 0 | 0 | 0 | + | + | + | 0? | 0 | 0 | + | + | + |
| Teratoca | 83-1881a | 0 | 0 | 0 | 0 | 0 | 0 | + | 0 | + | 0 | 0 | 0 |
| | 83-1881b | 0 | 0 | 0 | 0 | 0 | 0 | + | 0 | 0 | 0 | 0 | 0 |
| | 82-19590 | 0 | 0 | 0 | 0 | 0 | 0 | + | 0 | + | 0 | 0 | 0 |
| Nevus | 82-23735 | 0 | 0 | 0 | + | 0 | 0 | + | 0 | 0 | 0 | 0 | 0 |
| Melanosarc. | 82-16834 | + | 0 | 0 | + | 0 | 0 | + | 0 | 0 | 0 | 0 | 0 |
| Astrocytoma | grade I | 0 | 0 | 0 | + | 0 | 0 | 0 | 0 | 0 | 0 | 0 | 0 |
| | grade II | 0 | 0 | 0 | 0 | 0 | 0 | 0 | 0 | 0 | 0 | 0 | 0 |
| Lymphoma | 82-16027 | 0 | 0 | 0 | 0 | 0 | 0 | 0 | 0 | 0 | 0 | 0 | 0 |
| | 83-2542 | 0 | 0 | 0 | 0 | 0 | 0 | +? | 0 | 0 | 0 | 0 | 0 |
| | smooth muscle | + | 0 | 0 | 0 | 0 | 0 | 0? | 0 | 0 | 0 | 0 | 0 |
| | endothelial C. | + | 0 | 0 | 0 | 0 | 0 | 0? | 0 | 0 | 0 | 0 | 0 |
| | interstitial | 0 | + | 0 | 0 | 0 | 0 | 0? | 0 | 0 | 0 | 0 | 0 |
| | fibroblast | 0 | 0 | 0 | + | 0 | 0 | + | 0 | 0 | 0 | 0 | 0 |
| | connect. tis. | 0 | 0 | 0 | + | 0 | 0 | + | 0 | 0 | 0 | 0 | 0 |

Legend to Table II
Immunopathological reaction of monoclonal antibodies of
Ueda et al supra (*) and F23 mAb with frozen tumor or normal
human tissue sections by immunofluorescence.
For parts A & B frozen sections of normal human

TISSUE DISTRIBUTION OF THE MONOCLONAL ANTIBODIES OF THE KIDNEY
-continued tissue:
- 0 = no reaction
- ± = heterogeneous positive reaction within the tissue
- + = homogeneous positive reaction within the tissue For parts C & D - frozen sections of human tumors
- 0 = no reaction
- ± = heterogeneous reaction
- + = positive reaction Note:
- C68 = colon monoclonal antibody CLH68 (co-pending application Serial No. 474,415)
- C26 = colon monoclonal antibody HT29/26 (co-pending application supra)
- AJ8 = astrocytoma monoclonal antibody (Cairncross, et al. Proc. Nat'l. Acad. Sci. U.S.A. 1982) co-pending serial number 413,861.
- NL-1 = monoclonal antibody recognizing calla antigen in acute lymphocytic leukemia (Tanimoto)
- NL-22 = mAb (Tanimoto)
- Q-14 = melanoma antibody (co-pending application Serial #445,561)
- P170 = AJ2 astrocytoma (Cairncross, Supra)
- P130 = AJ2 astrocytoma (Cairncross, Supra)
- $S_6/S_{27}$ = refers to tests done using either $S_6$ or $S_{27}$ mAb which gives same reaction

TABLE IIB

Indirect immunofluorescence and immunoperoxidase analysis of frozen sections of 14-week fetal (F) and adult (A) normal tissues

| Organs/tissues/cells* | S4 F | S4 A | F23+ F | F23+ A | S23 F | S23 A | S27 F | S27 A | S22 F | S22 A | V1 F | V1 A |
|---|---|---|---|---|---|---|---|---|---|---|---|---|
| Kidney | | | | | | | | | | | | |
| glomerulus | ● | ● | ○ | ○ | ○ | ○ | ◐ | ○ | ○ | ○ | ◐ | ○ |
| proximal tubule | ● | ● | ● | ● | ● | ● | ● | ● | ○ | ○ | ○ | ○ |
| Henle's loop | | ◐ | | ○ | | ● | | ● | | ○ | | ○ |
| distal tubule | ○ | ○ | ○ | ○ | ○ | ○ | ○ | ○ | ○ | ○ | ○ | ○ |
| collecting duct | ○ | ○ | ○ | ○ | ○ | ○ | ◐ | ○ | ○ | ○ | ○ | ○ |
| Urothelium | ○ | ○ | ○ | ○ | ○ | ○ | ○ | ○ | ○ | ○ | ○ | ○ |
| Prostate | | ○ | | ○ | | ● | | ● | | ○ | | ○ |
| Testis-Leydig cells | ○ | ○ | ○ | ○ | ○ | ○ | ○ | ○ | ○ | ○ | ● | ○ |
| Breast | | ○ | | ○ | | ● | | ○ | | ○ | | ○ |
| Ovary theca | ○ | ○ | ○ | ○ | ○ | ○ | ○ | ○ | ○ | ○ | ○ | ● |
| Fallopian tube | ○ | ○ | ○ | ○ | ○ | ○ | ○ | ○ | ○ | ○ | ○ | ○ |
| Uterus/cervix | ○ | ○ | ○ | ○ | ○ | ○ | ○ | ○ | ○ | ○ | ○ | ○ |
| Placenta trophoblasts | ○ | | ○ | | ● | | ● | | ○ | | ○ | |
| Lung | ○ | ○ | ○ | ○ | ● | ○ | ○ | ○ | ○ | ○ | ○ | ○ |
| Esophagus | ○ | ○ | ○ | ○ | ○ | ○ | ○ | ○ | ○ | ○ | ○ | ○ |
| Stomach | ○ | ○ | ○ | ○ | ○ | ○ | ○ | ○ | ○ | ○ | ○ | ○ |
| Small intestine | ○ | ○ | ○ | ○ | ○ | ○ | ○ | ○ | ○ | ○ | ○ | ○ |
| Colon | ○ | ○ | ○ | ○ | ● | ●* | ○ | ○ | ○ | ○ | ○ | ○ |
| Pancreas | ○ | ○ | ○ | ○ | ○ | ○ | ○ | ○ | ○ | ○ | ○ | ○ |
| Liver | ○ | ○ | ○ | ○+ | ○ | ○ | ○ | ○ | ○ | ○ | ○ | ○ |
| Skin | ○ | ○ | ○ | ○ | ○ | ○ | ○ | ○ | ○ | ○ | ○ | ○ |
| Brain | ○ | ○ | ○ | ○ | ○ | ○ | ○ | ○ | ○ | ○ | ○ | ○ |
| Adrenal zona fasciculata | ○ | ○ | ○ | ○ | ○ | ○ | ○ | ○ | ○ | ○ | ● | ● |
| Thyroid | | ○ | | ○ | | ○ | | ○ | | ○ | | ○ |
| Lymph node | ○ | ○ | ○ | ○ | ○ | ○ | ○ | ○ | ○ | ○ | ○ | ○ |
| Spleen | ○ | ○ | ○ | ○ | ○ | ○ | ○ | ○ | ○ | ○ | ○ | ○ |
| Thymus | ○ | | ○ | | ○ | | ○ | | ○ | | ○ | |
| Heart | ○ | ○ | ○ | ○ | ○ | ○ | ○ | ○ | ○ | ○ | ○ | ○ |
| Muscle (smooth/striated) | ○ | ○ | ○ | ○ | ○ | ○ | ○ | ○ | ○ | ○ | ○ | ○ |
| Endothelial cells | ○ | ○ | ○ | ○ | ○ | ○ | ○ | ○ | ○ | ○ | ○ | ○ |
| Fibroblasts | ○ | ○ | ● | ● | ○ | ○ | ○ | ○ | ○ | ○ | ○ | ○ |
| Cartilage | ○ | ○ | ● | ● | ○ | ○ | ○ | ○ | ○ | ○ | ○ | ○ |
| Interstitial matrix | ● | ● | ○ | ○ | ○ | ○ | ○ | ○ | ○ | ○ | ○ | ○ |

●Strong fluorescence (++++ to ++): ◐weak fluorescence (+) and ○no fluorescence.
*Findings refer to epithelial cells in organs/tissues.
+F23 was detected in connective tissue of all organs examined and in liver bile canaliculi and ducts.

TABLE IIIA

Indirect immunofluorescence and immunoperoxidase analysis of frozen sections of human tumors and of cryopreserved leukemia and lymphoma cells

| Specimens | S4* | F23* | S23 | S27 | S22 | V1 | Specimens | S4* | F23* | S23 | S27 | S22 | V1 |
|---|---|---|---|---|---|---|---|---|---|---|---|---|---|
| Renal cell carcinoma | | | | | | | Lung epidermoid carcinoma | | | | | | |
| Primary (KC-12) | ● | ● | ●· | ● | ○ | ○ | Lung oat cell carcinoma | ○ | ● | ○ | ○ | ○ | ○ |
| Primary (KC-20) | ● | ● | ● | ● | ○ | ○ | Lung carcinoid | ○ | ○ | ○ | ○ | ○ | ○ |
| Primary (KC-21) | ● | ● | ● | ● | ○ | ○ | Ovarian carcinoma | ○ | ○ | ● | ○ | ○ | ○ |
| Primary (KC-23) | ● | ● | ●· | ● | ○ | ○ | | ○ | ○ | ● | ○ | ○ | ○ |
| Primary (KC-47) | ● | ● | ● | ● | ○ | ○ | | ○ | ○ | ● | ○ | ○ | ○ |
| Primary (KC-51) | ● | ● | ●· | ● | ○ | ○ | | ○ | ○ | ● | ○ | ○ | ○ |
| Primary (KC-62) | ● | ● | ● | ● | ○ | ○ | | ○ | ○ | ○ | ○ | ○ | ○ |
| Primary (KC-19) | ● | ● | ● | ● | ● | ○ | Prostatic adenocarcinoma | ○ | ○ | ○ | ○ | ○ | ○ |
| Primary (KC-36) | ● | ● | ○ | ● | ● | ○ | Liposarcoma | ○ | ○ | ● | ● | ○ | ○ |
| Primary (KC-44) | ● | ● | ●· | ● | ● | ○ | Leiomyosarcoma | ○ | ○ | ○ | ○ | ○ | ○ |
| Primary (KC-52) | ● | ● | ● | ● | ● | ○ | | ○ | ○ | ○ | ○ | ○ | ○ |
| Primary (KC-66) | ● | ● | ● | ● | ● | ○ | Rhabdomyosarcoma (embryonal) | ○ | ○ | ○ | ○ | ○ | ○ |
| | ○ | ○ | ● | ● | ● | ○ | | ○ | ○ | ○ | ○ | ○ | ○ |
| Primary (KC-10) | ● | ○ | ● | ● | ● | ○ | Rhabdomyosarcoma | ○ | ○ | ○ | ○ | ○ | ○ |
| Primary (KC-65) | ○ | ● | ● | ● | ● | ○ | Fibrosarcoma | ○ | ● | ○ | ○ | ○ | ○ |
| Primary (KC-63) | ○ | ● | ○ | ○ | ○ | ○ | Chondrosarcoma | ○ | ○ | ○ | ○ | ○ | ○ |
| Primary (KC-68) | ● | ● | ● | ● | ○ | ○ | | ● | ● | ○ | ·○ | ○ | ○ |
| Metastatic (KC-7) | ●· | ● | ● | ● | ● | ○ | | ● | ● | ○ | ○ | ○ | ○ |
| Metastatic (KC-24) | ● | ● | ●· | ● | ● | ○ | Osteogenic sarcoma | ● | ● | ○ | ○ | ○ | ○ |
| Metastatic (KC-29) | ● | ● | ●· | ●· | ○ | ○ | Sarcoma (spindle cell) | ● | ○ | ○ | ○ | ○ | ○ |
| Metastatic (KC-53) | ○ | ● | ● | ● | ○ | ○ | Mesothelioma (lung) | ● | ○ | ○ | ○ | ○ | ○ |
| Transitional cell carcinoma | | | | | | | | ○ | ● | ○ | ○ | ○ | ○ |
| Renal pelvis (XXX) | ○ | ○ | ●· | ○ | ○ | ○ | | ○ | ● | ○ | ○ | ○ | ○ |
| Renal pelvis (XXX) | ○ | ○ | ○ | ○ | ○ | ○ | Nerves | ○ | ● | ○ | ○ | ○ | ○ |
| Ureter | ○ | ○ | ●· | ○ | ○ | ○ | Melanoma | ○ | ● | ○ | ○ | ○· | ●○ |
| Bladder (XXX) | ○ | ○ | ○ | ○ | ○ | ○ | | ○ | ● | ○ | ○ | ○ | ○ |
| Bladder (XXX) | ○ | ○ | ○ | ○ | ○ | ○ | | ○ | ● | ○ | ○ | ○ | ○ |
| Bladder (XXX) | ○ | ○ | ○ | ○ | ○ | ○ | | ○ | ○ | ○ | ○ | ○ | ○ |
| Bladder (XXX) | ○ | ○ | ○ | ○ | ● | ○ | | ○ | ○ | ○ | ○ | ○ | ○ |
| Bladder (XXX) | ○ | ○ | ○ | ○ | ● | ● | Germ cell tumor (embryonal) | ○ | ○ | ○ | ○ | ○ | ○ |
| Adrenal cortical carcinoma | ○ | ○ | ○ | ○ | ○ | ● | | ○ | ○ | ○ | ○ | ○ | ○ |
| | ○ | ○ | ○ | ○ | ○ | ○ | Seminoma | ○ | ○ | ○ | ○ | ○ | ○ |
| Breast fibroadenoma | ○ | ● | ○ | ○ | ○ | ○ | B-cell leukemia | ○ | ●· | ○ | ○ | ○ | ○ |
| | ○ | ○ | ○ | ○ | ○ | ○ | | ○ | ○ | ○· | ●· | ○ | ○ |
| Breast adenocarimoma | ○ | ○ | ○ | ○ | ○ | ○ | T-cell leukemia | ○ | ○ | ●· | ●· | ○ | ○ |
| | ○ | ○ | ○ | ○ | ○ | ○ | | ○ | ○ | ○ | ○ | ○ | ○ |
| | ○ | ○ | ● | ○ | ○ | ○ | Null-cell leukemia | ○ | ○ | ○ | ●· | ○ | ○ |
| Colon adenoma | ○ | ○ | ● | ○ | ○ | ○ | | ○ | ○ | ○ | ○ | ○ | ○ |
| | ○ | ○ | ○ | ○ | ○ | ○ | | ○ | ○ | ○ | ○ | ○ | ○ |
| Colon adenocarcinoma | ○ | ○ | ○ | ○ | ○ | ○ | Acute myelogenous leukemia | ○ | ○ | ○ | ○ | ○ | ○ |
| | ○ | ○ | ○ | ○ | ○ | ○ | | ○ | ○ | ○ | ○ | ○ | ○· |
| | ○ | ● | ●· | ○ | ○ | ○ | B-cell lymphoma | ○ | ● | ●· | ●· | ○ | ○ |
| Lung epidermoid carcinoma | ○ | ○ | ○ | ○ | ○ | ○ | T cell lympohoma | ○ | ○ | ○ | ●· | ○ | ○ |

●, Strong fluorescence (++++ to ++); ●, weak fluorescence (+);, no fluorescence; , heterogeneous pattern of antigen expression.
*S4 was detected in the vessels and intersititial matrix of tumors.
*F23 was detected in connective tissue of tumors.

TABLE IIIB

Renal Carcinoma Typing Using Monoclonal Antibody

| Patient # | Chart | Renal Pathol. | Surg. Date | Stage | Met Site | S4 | S22 | S23 | S27 |
|---|---|---|---|---|---|---|---|---|---|
| 1 | 785198 | 816328 | 0481 | 1 | | + | ± | + | + |
| 2 | 808371 | 8218413 | 1082 | 1 | | + | − | + | + |
| 3 | 799223 | 824878 | 0382 | 1 | | + | − | − | + |
| 4 | 791203 | 8115565 | 0881 | 1 | | + | − | − | + |
| 5 | 736676 | 818362 | 0581 | 1 | | − | − | + | + |
| 6 | 812434 | 83578 | 0182 | 1 | | + | − | + | + |
| 7 | 797121 | 822197 | 0282 | 1 | | + | − | + | + |
| 8 | 992833 | 8118815 | 1081 | 1 | | − | − | + | + |
| 9 | 572899 | 829219 | 0582 | 1 | | − | + | + | + |
| 10 | 991626 | 8116180 | 0981 | 1 | | − | − | − | − |
| 11 | 810260 | 822093 | 1182 | 1 | | + | ± | + | + |
| 12 | 799817 | 8113368 | 0781 | 1 | | + | − | − | + |
| 13 | 796815 | 82773 | 0182 | 1 | | + | − | − | + |
| 14 | 787807 | 8116150 | 0981 | 2 | | + | ± | + | + |
| 15 | 787964 | 8110339 | 0681 | 2 | | + | − | − | + |
| 16 | 788328 | 8110924 | 0681 | 2 | | − | ± | + | + |
| 17 | 798926 | 823741 | 0382 | 2 | | + | − | + | + |
| 18 | 543708 | 824937 | 0382 | 2 | | + | ± | − | + |
| 19 | 643512 | 823179 | | 2 | | + | ± | + | + |
| 20 | 991637 | 8116440 | 0981 | 2 | | − | − | − | + |
| 21 | 792783 | 8121194 | 1181 | 2 | | + | ± | + | + |

TABLE IIIB-continued
Renal Carcinoma Typing Using Monoclonal Antibody

| Patient # | Chart | Renal Pathol. | Surg. Date | Stage | Met Site | S4 | S22 | S23 | S27 |
|---|---|---|---|---|---|---|---|---|---|
| 22 | 801696 | 8827564 | 0482 | 4 | | − | − | − | − |
| 23 | 799512 | 824468 | 0382 | 2 | | + | ± | + | + |
| 24 | 787183 | 819786 | 0681 | 2 | | + | + | + | + |
| 25 | 802482 | 8210362 | 0682 | 3 | | + | − | − | − |
| 26 | 795288 | 8122239 | 1281 | 3 | | − | + | − | + |
| 27 | 790003 | 8114712 | 0881 | 4 | | − | − | − | + |
| 28 | 784799 | 815643 | 0481 | 4 | | − | − | − | + |
| 29 | 788722 | 811186 | 0681 | 4 | | − | − | − | + |
| 30 | 786021 | 819070 | 0581 | 4 | | + | + | + | + |
| 31 | 802850 | 829377 | 0582 | 4 | | + | − | − | + |
| 32 | 784690 | 816654 | 0481 | 4 | | + | − | − | + |
| 33 | 787833 | 8110396 | 0681 | 4 | | − | − | − | + |
| 34 | 991686 | 8117874 | 1081 | 4 | | − | + | − | + |
| 35 | 806154 | 8215512 | 0882 | 4 | | − | − | − | − |
| 36 | 784902 | 816649 | 0481 | 3 | | − | + | + | + |
| 37 | 993395 | 8215363 | 0882 | 1 | | + | − | + | + |
| 38 | 993395 | 832130 | 0282 | 2 | | + | − | + | + |
| 39 | 738554 | 0 | 1082 | 4 | | − | − | + | + |
| 40 | 738554 | 0 | 1182 | 4 | | − | − | + | + |
| 41 | 738554 | 0 | 1282 | 4 | SKULL | − | − | + | + |
| 42 | 0 | 806807 | 1082 | 2 | | + | − | + | + |
| 43 | 794184 | 8222884 | | 4 | SKIN | − | + | + | + |
| 44 | 794184 | 0 | | 4 | SKIN | − | + | + | + |
| 45 | 794184 | 0 | | 4 | SKIN | − | + | + | + |
| 46 | 654004 | 818164 | 0581 | 4 | BONE | + | ± | − | + |
| 47 | 654004 | 0 | | 4 | BONE | + | ± | − | + |
| 48 | 794954 | 829571 | 0582 | 4 | BRAIN | + | − | − | + |
| 49 | 785655 | 816867 | 0481 | 4 | BONE | + | − | − | + |
| 50 | 791592 | 8116033 | 0981 | 4 | BONE | + | − | − | + |
| 51 | 786081 | 8111741 | 0781 | 4 | BONE | − | ± | − | + |
| 52 | 991879 | 823468 | 0382 | 4 | LUNG | + | − | + | + |
| 53 | 808557 | 8219016 | 1082 | 4 | NODES | − | − | − | + |
| 54 | 814996 | 838182 | 0283 | 4 | | + | − | − | + |
| 55 | 807399 | 8216668 | 0982 | 4 | | − | − | − | + |

Legend to Table III:
Frozen sections of renal carcinoma (RC) specimens are typed with the four mouse monoclonal antibodies $S_4$, $S_{22}$, $S_{23}$ and $S_{27}$ (derived from SK-RC-7 immunizing cell line) using standard immunofluorescence and peroxidase techniques.
Met Site = site of metastisis specimen
+ = positive reaction
− = negative reaction
± = heterogeneous reaction
Patient 38, 40 and 41 concern different tissue specimens from the same patient i.e. different sites. This applies to 46, 47 and 48 as well.

TABLE IV
Derivation and Characterization of Eleven Mouse Monoclonal Antibodies Detecting Cell Surface Antigens of Human Renal Cancer.

| Designation (Ig subclass) | Immunizing Cell Type | Molecular Weight of Antigen (Reference) | Chromosome Assignment of Locus Coding for Antigen (Reference) |
|---|---|---|---|
| mAbQ14 (γ1) | SK-MEL-28 Melanoma | Mr130,000 (gp 130) (140) | Chromosome 11 (147) |
| mAbJ143 (γ1) | 253J Bladder Cancer | Mr complex (142) (gp140/120/30) | Chromosome 17 (147) |
| mAbAJ8 (γ1) | SK-MG-1 Astrocytoma | Mr100,000 (gp100)(140) | not known |
| mAbS4 (γ2a) | SK-RC-7 Renal Cancer | Mr160,000 (gp160)(118) | not known |
| mAbF23 (γ2a) | Normal Kidney Epithelium | Mr140,000 (gp140)(119) | Chromosome 15 (147) |
| mAbS23 (γ1) | SK-RC-7 Renal Cancer | Mr120,000 (gp120r)(118) | Chromosome 2* (148) |
| mAbS27 (γ1) | SK-RC-7 Renal Cancer | Mr120,000 (gp120nr)(118) | Chromosome 2* (148) |
| mAbC26 (γ2a) | HT-29 Colon Cancer | Mr40,000/28,000 (gp40)(143) | not known |
| mAbT16 (γ2b) | T24 Bladder Cancer | Mr48,000/42,000 (gp48/42)(142) | not known |
| mAbS22 (γ1) | SK-RC-7 Renal Cancer | Mr115,000 (gp115)(118) | not known |
| mAbV1 (γ1) | SK-RC-6 Renal Cancer | Heat Stable (118) | Chromosome 12 (149) |

*Based on finding that mAbS23 and mAbS27 detect epitopes on the adenosine deaminase binding protein (148, unpublished observations).

TABLE V
Localization of cell surface antigens defined by mouse monoclonal antibodies (mAbs) on the normal adult nephron.*

| mAb | Glomerulus | Proximal Tubule | Henle's Loop | Distal Tubule | Collecting Duct | Urothelium |
|---|---|---|---|---|---|---|
| Q14 | — | | | | | |
| J143+ | — | | | | | |
| AJ8 | — | | | | | |

TABLE V-continued

Localization of cell surface antigens defined by mouse monoclonal antibodies (mAbs) on the normal adult nephron.*

| mAb | Glomerulus | Proximal Tubule | Henle's Loop | Distal Tubule | Collecting Duct | Urothelium |
|---|---|---|---|---|---|---|
| S4§ | ———————————————— | | | | | |
| F23ƒ | ———————— | | | | | |
| S27 | | ———————————— | | | | |
| C26 | | | | ———————————————— | | |
| T16 | | | | ———————————— | | |
| S22Σ | | | | | | |
| V1^ | | | | | | |

*The techniques used to localize antigen expression were indirect immunofluorescence and indirect immunoperoxidase. Bar: presence of antigen; bar width: intensity of staining.
+Expressed on basement membrane.
§Also expressed on vessels and interstitial matrix between tubules in medulla.
ƒAlso found on fibrocytes between tubule cells and fibrous capsule.
ΣExpressed only on a subset of renal cancers.
^Expressed on adrenal, testis, ovary.

TABLE VI

Indirect Immunofluorescence and Immunoperoxidase Analysis of Frozen Sections of 14 Week Fetal (F) and Adult (A) Normal Tissues.

| Organs/Tissues/Cells* | S4+ F | S4+ A | F23§ F | F23§ A | S23 F | S23 A | S27 F | S27 A | S22 F | S22 A | V1 F | V1 A |
|---|---|---|---|---|---|---|---|---|---|---|---|---|
| Kidney | | | | | | | | | | | | |
| glomerulus | ● | ● | 0 | 0 | 0 | 0 | 0 | 0 | 0 | 0 | 0 | 0 |
| proximal tubule | ● | ● | ● | ● | ● | ● | ● | ● | 0 | 0 | 0 | 0 |
| Henle's loop | | 0 | | 0 | | ● | | ● | | 0 | | 0 |
| distal tubule | 0 | 0 | 0 | 0 | 0 | 0 | 0 | 0 | 0 | 0 | 0 | 0 |
| collecting duct | 0 | 0 | 0 | 0 | 0 | 0 | 0 | 0 | 0 | 0 | 0 | 0 |
| Urothelium | 0 | 0 | ● | 0 | 0 | 0 | 0 | 0 | 0 | 0 | 0 | 0 |
| Prostate | | 0 | | 0 | | ● | | ● | | 0 | | 0 |
| Testis-Leydig cells | 0 | 0 | 0 | 0 | 0 | 0 | 0 | 0 | 0 | 0 | ● | 0 |
| Breast | | 0 | | 0 | | ● | | 0 | | 0 | | 0 |
| Ovary-theca | 0 | 0 | 0 | 0 | 0 | 0 | 0 | 0 | 0 | 0 | 0 | ● |
| Fallopian Tube | 0 | 0 | 0 | 0 | 0 | 0 | 0 | 0 | 0 | 0 | 0 | 0 |
| Uterus/Cervix | 0 | 0 | 0 | 0 | 0 | 0 | 0 | 0 | 0 | 0 | 0 | 0 |
| Placenta-trophoblasts | 0 | | 0 | | ● | | ● | | 0 | | 0 | |
| Lung | 0 | 0 | 0 | 0 | ● | 0 | 0 | 0 | 0 | 0 | 0 | 0 |
| Esophagus | 0 | 0 | 0 | 0 | 0 | 0 | 0 | 0 | 0 | 0 | 0 | 0 |
| Stomach | 0 | 0 | 0 | 0 | 0 | 0 | 0 | 0 | 0 | 0 | 0 | 0 |
| Small Intestine | 0 | 0 | 0 | 0 | 0 | 0 | 0 | 0 | 0 | 0 | 0 | 0 |
| Colon | 0 | 0 | 0 | 0 | ● | ● | 0 | 0 | 0 | 0 | 0 | 0 |
| Pancreas | 0 | 0 | 0 | 0 | 0 | 0 | 0 | 0 | 0 | 0 | 0 | 0 |
| Liver | 0 | 0 | 0 | 0§ | 0 | 0 | 0 | 0 | 0 | 0 | 0 | 0 |
| Skin | 0 | 0† | 0 | 0 | 0 | 0 | 0 | 0 | 0 | 0 | 0 | 0 |
| Brain | 0 | 0 | 0 | 0 | 0 | 0 | 0 | 0 | 0 | 0 | 0 | 0 |
| Adrenal-zona fasciculata | 0 | 0 | 0 | 0 | 0 | 0 | 0 | 0 | 0 | 0 | ● | ● |
| Thyroid | | 0 | | 0 | | 0 | | 0 | | 0 | | 0 |
| Lymph Node | 0 | 0 | 0 | 0 | 0 | 0 | 0 | 0 | 0 | 0 | 0 | 0 |
| Spleen | 0 | 0 | 0 | 0 | 0 | 0 | 0 | 0 | 0 | 0 | 0 | 0 |
| Thymus | 0 | | 0 | | 0 | | 0 | | 0 | | 0 | |
| Heart | 0 | 0 | 0 | 0 | 0 | 0 | 0 | 0 | 0 | 0 | 0 | 0 |
| Muscle-smooth/striated | 0 | 0 | 0 | 0 | 0 | 0 | 0 | 0 | 0 | 0 | 0 | 0 |
| Endothelial Cells | 0 | 0 | 0 | 0 | 0 | 0 | 0 | 0 | 0 | 0 | 0 | 0 |
| Fibroblasts | 0 | 0 | ● | ● | 0 | 0 | 0 | 0 | 0 | 0 | 0 | 0 |
| Cartilage | 0 | 0 | ● | ● | 0 | 0 | 0 | 0 | 0 | 0 | 0 | 0 |
| Interstitial Matrix | ● | ● | 0 | 0 | 0 | 0 | 0 | 0 | 0 | 0 | 0 | 0 |

Legend: ●: strong fluorescence (++++ to ++). ●': weak fluorescence (+), or 0: no fluorescence.
*Findings refer to epithelial cells in organs/tissues.
+ S4 is detected in vessels and interstitial matrix of organs. A matrix staining was observed around sweat glands and hair follicles in skin.
§ F23 is detected in connective tissue of all organs examined. A positive staining was detected in bile canuliculi and ducts (luminal surface) in liver.

TABLE VII

Indirect Immunofluorescence and Immunoperoxidase Analysis of Frozen Sections of 14 Week Fetal (F) and Adult (A) Normal Tissues.

| Organs/Tissues/Cells* | Q14+ F | Q14+ A | J143 F | J143 A | AJ8 F | AJ8 A | C26 F | C26 A | T16 F | T16 A |
|---|---|---|---|---|---|---|---|---|---|---|
| Kidney | | | | | | | | | | |
| glomerulus | ● | ● | ●+ | ●+ | ● | ● | 0 | 0 | 0 | 0 |
| proximal tubule | 0 | 0 | 0 | 0 | ● | ● | ● | 0 | 0 | 0 |
| Henle's loop | | 0 | | 0 | | ● | | ● | | ● |
| distal tubule | 0 | 0 | 0 | 0 | 0 | 0 | ● | ● | ● | ● |

TABLE VII-continued

Indirect Immunofluorescence and Immunoperoxidase Analysis of Frozen Sections of 14 Week Fetal (F) and Adult (A) Normal Tissues.

| | Monoclonal Antibodies | | | | | | | | | |
|---|---|---|---|---|---|---|---|---|---|---|
| | Q14+ | | J143 | | AJ8 | | C26 | | T16 | |
| Organs/Tissues/Cells* | F | A | F | A | F | A | F | A | F | A |
| collecting duct | 0 | 0 | ●+ | ●+ | 0 | 0 | ● | ● | ● | ● |
| Urothelium | 0 | 0 | ● | ● | 0 | 0 | ● | 0 | ● | ● |
| Prostate | | 0 | | ●+ | | 0 | | ● | | ● |
| Testis-Leydig cells | 0 | 0 | 0 | 0 | 0 | 0 | 0 | 0 | 0 | 0 |
| Breast | | 0 | | ●+ | | ● | | ● | | ● |
| Ovary-theca | 0 | 0 | 0 | 0 | 0 | 0 | 0 | 0 | 0 | 0 |
| Fallopian Tube | 0 | 0 | 0 | 0 | 0 | 0 | ● | ● | 0 | 0 |
| Uterus/Cervix | 0 | 0 | ● | ● | 0 | 0 | ● | ● | ● | ● |
| Placenta-trophoblasts | 0 | | ●+ | | 0 | | ● | | ● | |
| Lung | 0 | 0 | 0 | 0 | 0 | 0 | ● | ● | 0 | 0 |
| Esophagus | 0 | 0 | ● | ● | 0 | 0 | ● | 0 | 0 | ● |
| Stomach | 0 | 0 | 0 | 0 | 0 | 0 | 0 | 0 | 0 | 0 |
| Small Intestine | 0 | 0 | 0 | 0 | 0 | 0 | 0 | 0 | 0 | 0 |
| Colon | 0 | 0 | 0 | 0 | ● | 0 | ● | ● | 0 | 0 |
| Pancreas | 0 | 0 | 0 | 0 | 0 | 0 | ● | ● | 0 | 0 |
| Liver | 0 | 0 | 0 | 0 | 0 | 0 | ● | ● | 0 | 0 |
| Skin | 0 | 0 | ● | ● | 0 | 0 | ● | ● | ● | ● |
| Brain | 0 | 0 | 0 | 0 | 0 | 0 | 0 | 0 | 0 | 0 |
| Adrenal-zona fasciculata | 0 | 0 | 0 | 0 | 0 | 0 | 0 | 0 | 0 | 0 |
| Thyroid | | 0 | | ●+ | | 0 | | 0 | | 0 |
| Lymph Node | 0 | 0 | 0 | 0 | 0 | 0 | 0 | 0 | 0 | 0 |
| Spleen | 0 | 0 | 0 | 0 | 0 | 0 | 0 | 0 | 0 | 0 |
| Thymus | 0 | | 0 | | 0 | | ● | | 0 | |
| Heart | 0 | 0 | 0 | 0 | 0 | 0 | 0 | 0 | 0 | 0 |
| Muscle-smooth/striated | ● | ● | ● | ● | 0 | 0 | 0 | 0 | 0 | 0 |
| Endothelial Cells | ● | ● | 0 | 0 | 0 | 0 | 0 | 0 | 0 | 0 |
| Fibroblasts | 0 | 0 | 0 | 0 | 0 | 0 | 0 | 0 | 0 | 0 |
| Cartilage | 0 | 0 | 0 | 0 | 0 | 0 | 0 | 0 | 0 | 0 |
| Interstitial Matrix | 0 | 0 | ●+ | ●+ | 0 | 0 | 0 | 0 | 0 | 0 |

Legend: ● : strong fluorescence (++++ to ++), ● : weak fluorescence (+), 0: heterogeneous patter, 0+: basement membrane patter or 0: no fluorescence.
*Findings refer to epithelial cells in organs/tissue.
+: Q14 is detected in smooth muscle of organs.

TABLE VIII

Indirect Immunofluorescence and Immunoperoxidase Analysis of Frozen Sections of Human Fetal Kidney.

| Fetal Kidney | Monoclonal Antibody | | | | | | | |
|---|---|---|---|---|---|---|---|---|
| | Q14 | J143 | AJ8 | S4 | F23 | S27 | C26 | T16 |
| Stage 0 - Pre Induction (7 week) | | | | | | | | |
| Mesonephros | | | | | | | | |
| Glomerulus | ● | ●+ | ● | ● | 0 | 0 | 0 | 0 |
| Proximal Tubule | 0 | 0 | ● | ● | ● | ● | ● | 0 |
| Distal Tubule | 0 | 0 | 0 | 0 | 0 | 0 | ● | ● |
| Wolffian Duct | 0 | ●+ | 0 | 0 | 0 | 0 | ● | ● |
| Metanephros | | | | | | | | |
| Mesenchyme | 0 | 0 | 0 | 0 | ● | 0 | 0 | 0 |
| Ureter Bud | 0 | 0 | 0 | 0 | 0 | 0 | ● | ● |
| Stage 1 - Blastema Stage (8, 11 week) | | | | | | | | |
| Metanephros | | | | | | | | |
| Mesenchyme | ● | 0 | 0 | 0 | ●' | 0 | 0 | 0 |
| Blastema | 0 | 0 | 0 | 0 | 0 | 0 | ● | 0 |
| Ureter Bud | 0 | ●+ | 0 | 0 | 0 | 0 | ● | ● |
| Stage 2 - Comma-shaped Tubule (8, 11, 14 week) | | | | | | | | |
| Metanephros | | | | | | | | |
| Mesenchyme | ● | 0 | 0 | 0 | ● | 0 | 0 | 0 |
| Developing Glomerulus | ● | ●+ | 0 | 0 | 0 | ●' | ● | 0 |
| Developing Tubule | 0 | ●+ | 0 | 0 | 0 | ●' | ● | 0 |
| Ureter Bud | 0 | ●+ | 0 | 0 | 0 | 0 | ● | ● |
| Stage 3 - S-shaped Tubule (11, 14, 22 week) | | | | | | | | |
| Metanephros | | | | | | | | |
| Glomerulus | ●' | ●+ | 0 | 0 | 0 | 0 | 0 | 0 |
| Proximal Tubule | 0 | ●+ | 0 | 0 | ● | ● | ●' | 0 |
| Distal Tubule | 0 | ●+ | 0 | 0 | 0 | 0 | ● | ●' |
| Collecting Duct | 0 | ●+ | 0 | 0 | 0 | 0 | ● | ● |
| Interstitial Tissue | 0 | 0 | 0 | 0 | ● | 0 | 0 | 0 |
| Stage 4 - Capillary Loop Stage (14, 22 week) | | | | | | | | |
| Metanephros | | | | | | | | |
| Glomerulus | ●' | ●+ | ● | ● | 0 | 0 | 0 | 0 |
| Proximal Tubule | 0 | 0 | ● | ● | ● | ● | ●' | 0 |
| Henle's Loop | 0 | 0 | 0 | 0 | 0 | ● | ● | ● |
| Distal Tubule | 0 | 0 | 0 | 0 | 0 | 0 | ● | ● |

TABLE VIII-continued

Indirect Immunofluorescence and Immunoperoxidase Analysis of Frozen Sections of Human Fetal Kidney.

| Fetal Kidney | Monoclonal Antibody | | | | | | | |
|---|---|---|---|---|---|---|---|---|
| | Q14 | J143 | AJ8 | S4 | F23 | S27 | C26 | T16 |
| Collecting Duct | 0 | + | 0 | | 0 | 0 | 0 | |
| Interstitial Tissue | 0 | | 0 | 0 | | | 0 | 0 | 0 |

Legend: ●: Strong fluorescence (++++ to ++), ': weak fluorescence (+), 0: no fluorescence, : heterogeneous pattern and +: Basement membrane pattern of antigen expression.

TABLE IXa

Indirect Immunoflorescence and Immunoperoxidase Analysis of Frozen Sections of Human Tumors and of Cryopreserved Leukemia and Lymphoma Cells.

| Specimens | Monoclonal Antibodies | | | | | |
|---|---|---|---|---|---|---|
| | S4* | F23+ | S23 | S27 | S22 | V1 |
| Renal Cell Carcinoma-primary (KC-12) | ●' | ● | ●' | ● | 0 | 0 |
| Renal Cell Carcinoma-primary (KC-20) | ● | ● | ● | ● | 0 | 0 |
| Renal Cell Carcinoma-primary (KC-21) | ● | ● | ● | ● | 0 | 0 |
| Renal Cell Carcinoma-primary (KC-23) | ● | ● | ● | ● | 0 | 0 |
| Renal Cell Carcinoma-primary (KC-47) | ● | ● | ● | ● | 0 | 0 |
| Renal Cell Carcinoma-primary (KC-51) | ● | ● | ●' | ● | 0 | 0 |
| Renal Cell Carcinoma-primary (KC-62) | ● | ● | ● | ● | 0 | 0 |
| Renal Cell Carcinoma-primary (KC-19) | ● | ● | ● | ● | ● | 0 |
| Renal Cell Carcinoma-primary (KC-36) | ● | ● | ● | ● | ● | 0 |
| Renal Cell Carcinoma-primary (KC-44) | ● | ● | ●' | ● | ● | 0 |
| Renal Cell Carcinoma-primary (KC-52) | ● | ● | ●' | ● | ● | 0 |
| Renal Cell Carcinoma-primary (KC-66) | ● | ● | ● | ● | ● | 0 |
| Renal Cell Carcinoma-primary (KC-10) | 0 | 0 | ● | ● | ● | 0 |
| Renal Cell Carcinoma-primary (KC-65) | ● | 0 | ● | ● | ● | 0 |
| Renal Cell Carcinoma-primary (KC-63) | 0 | ● | ● | ● | ● | 0 |
| Renal Cell Carcinoma-primary (KC-68) | 0 | ● | 0 | ● | ● | 0 |
| Renal Cell Carcinoma-metastatic (KC-7) | ● | ● | ● | ● | 0 | 0 |
| Renal Cell Carcinoma-metastatic (KC-24) | ●' | ● | ● | ● | ● | 0 |
| Renal Cell Carcinoma-metastatic (KC-29) | ● | ● | ●' | ● | ● | 0 |
| Renal Cell Carcinoma-metastatic (KC-53) | 0 | ● | ●' | ●' | 0 | 0 |
| Transitional Cell Carcinoma (Renal pelvis) | 0 | 0 | ●' | 0 | 0 | 0 |
| Transitional Cell Carcinoma (Renal pelvis) | 0 | 0 | 0 | 0 | 0 | 0 |
| Transitional Cell Carcinoma (Ureter) | 0 | 0 | 0 | 0 | 0 | 0 |
| Transitional Cell Carcinoma (Bladder) | 0 | 0 | ●' | 0 | 0 | 0 |
| Transitional Cell Carcinoma (Bladder) | 0 | 0 | 0 | 0 | 0 | 0 |
| Transitional Cell Carcinoma (Bladder) | 0 | 0 | 0 | 0 | 0 | 0 |
| Transitional Cell Carcinoma (Bladder) | 0 | 0 | 0 | 0 | 0 | 0 |
| Transitional Cell Carcinoma (Bladder) | 0 | 0 | 0 | 0 | 0 | 0 |
| Adrenal Cortical Carcinoma | 0 | 0 | 0 | 0 | ● | 0 |
| Adrenal Cortical Carcinoma | 0 | 0 | 0 | 0 | 0 | ● |
| Breast Fibroadenoma | 0 | 0 | 0 | 0 | 0 | 0 |
| Breast Fibroadenoma | 0 | 0 | 0 | 0 | 0 | 0 |
| Breast Adenocarcinoma-primary | 0 | ● | 0 | 0 | 0 | 0 |
| Breast Adenocarcinoma-primary | 0 | 0 | 0 | 0 | 0 | 0 |
| Breast Adenocarcinoma-metastatic | 0 | 0 | 0 | 0 | 0 | 0 |
| Colon Adenoma | 0 | 0 | 0 | 0 | 0 | 0 |
| Colon Adenoma | 0 | 0 | ● | 0 | 0 | 0 |
| Colon Adenocarcinoma | 0 | 0 | ● | 0 | 0 | 0 |
| Colon Adenocarcinoma | 0 | 0 | ● | 0 | 0 | 0 |
| Colon Adenocarcinoma | 0 | 0 | 0 | 0 | 0 | 0 |
| Lung Epidermoid Carcinoma | 0 | 0 | 0 | 0 | 0 | 0 |
| Lung Epidermoid Carcinoma | 0 | ● | ●' | 0 | 0 | 0 |
| Lung Epidermoid Carcinoma | 0 | 0 | 0 | 0 | 0 | 0 |
| Lung Oat Cell Carcinoma | 0 | 0 | 0 | 0 | 0 | 0 |
| Lung Carcinoid | 0 | 0 | 0 | 0 | 0 | 0 |
| Ovarian Carcinoma | 0 | 0 | ● | 0 | 0 | 0 |
| Ovarian Carcinoma | 0 | 0 | ● | 0 | 0 | 0 |
| Ovarian Carcinoma | 0 | 0 | ● | 0 | 0 | 0 |
| Ovarian Carcinoma | 0 | 0 | 0 | 0 | 0 | 0 |
| Ovarian Carcinoma | 0 | 0 | 0 | 0 | 0 | 0 |
| Prostatic Adenocarcinoma | 0 | 0 | ● | ● | 0 | 0 |
| Liposarcoma | 0 | 0 | 0 | 0 | 0 | 0 |
| Leiomyosarcoma | 0 | 0 | 0 | 0 | 0 | 0 |
| Leiomyosarcoma | 0 | 0 | 0 | 0 | 0 | 0 |
| Rhabdomyosarcoma (Embryonal) | 0 | 0 | 0 | 0 | 0 | 0 |
| Rhabdomyosarcoma | 0 | 0 | 0 | 0 | 0 | 0 |
| Fibrosarcoma | 0 | ● | 0 | 0 | 0 | 0 |
| Chondrosarcoma | ● | 0 | 0 | 0 | 0 | 0 |
| Chondrosarcoma | 0 | ● | 0 | 0 | 0 | 0 |
| Chondrosarcoma | ● | 0 | 0 | 0 | 0 | 0 |
| Osteogenic Sarcoma | ● | ● | 0 | 0 | 0 | 0 |
| Sarcoma (Spindle Cell) | ● | 0 | 0 | 0 | 0 | 0 |
| Mesothelioma (Lung) | ● | 0 | 0 | 0 | 0 | 0 |
| Astrocytoma-stage I | 0 | ● | 0 | 0 | 0 | 0 |

TABLE IXa-continued

Indirect Immunoflorescence and Immunoperoxidase Analysis of Frozen Sections of Human Tumors and of Cryopreserved Leukemia and Lymphoma Cells.

| Specimens | Monoclonal Antibodies | | | | | |
|---|---|---|---|---|---|---|
| | S4* | F23+ | S23 | S27 | S22 | V1 |
| Astrocytoma-stage III | 0 | 0 | 0 | 0 | 0 | •0 |
| Nevus | 0 | ● | 0 | 0 | 0 | 0 |
| Melanoma-primary | 0 | 0 | 0 | 0 | 0 | 0 |
| Melanoma-primary | 0 | ● | 0 | 0 | 0 | 0 |
| Melanoma-metastatic | 0 | 0 | 0 | 0 | 0 | 0 |
| Melanoma-metastatic | 0 | 0 | 0 | 0 | 0 | 0 |
| Melanoma-metastatic | 0 | 0 | 0 | 0 | 0 | 0 |
| Germ Cell Tumor (Embryonal) | 0 | 0 | 0 | 0 | 0 | 0 |
| Germ Cell Tumor (Embryonal) | 0 | 0 | 0 | 0 | 0 | 0 |
| Germ Cell Tumor (Seminoma) | 0 | 0 | 0 | 0 | 0 | 0 |
| B Cell Leukemia | 0 | ●' | 0 | 0 | 0 | 0 |
| B Cell Leukemia | 0 | 0 | 0 | ●' | 0 | 0 |
| T Cell Leukemia | 0 | 0 | ●' | ●' | 0 | 0 |
| T Cell Leukemia | •0 | 0 | 0 | 0 | 0 | 0 |
| Null Cell Leukemia | 0 | 0 | 0 | 0 | 0 | 0 |
| Null Cell Leukemia | 0 | 0 | 0 | ●' | 0 | 0 |
| Null Cell Leukemia | 0 | 0 | 0 | 0 | .0 | 0 |
| Acute Myelogenous Leukemia | 0 | 0 | 0 | 0 | 0 | 0 |
| Acute Myelogenous Leukemia | 0 | 0 | 0 | 0 | 0 | 0 |
| B Cell Lymphoma | 0 | 0 | 0 | 0 | 0 | 0 |
| B Cell Lymphoma | 0 | ●' | ●' | ●' | 0 | 0 |
| T Cell Lymphoma | 0 | 0 | 0 | ●' | 0 | 0 |

Legend: Strong fluorescence (++++ to ++), ' weak fluorescence (+), 0 no fluorescence or heterogeneous patter of antigen expression.
*S4 is detected in the vessles and interstitial matrix of tumors.
+ F23 is detected in connective tissue of tumors.

TABLE IXb

Indirect Immunofluorescence and Immunoperoxidase Analysis of Frozen Sections of Human Tumors and of Cryopreserved Leukemia and Lymphoma Cells.

| Specimens | Monoclonal Antibodies | | | | |
|---|---|---|---|---|---|
| | *Q14 | J143 | AJ8 | C26 | T16 |
| Renal Cell Carcinoma-primary (KC-12) | 0 | ●+ | 0 | 0 | 0 |
| Renal Cell Carcinoma-primary (KC-20) | 0 | 0 | 0 | 0 | 0 |
| Renal Cell Carcinoma-primary (KC-21) | 0 | ● | 0 | 0 | 0 |
| Renal Cell Carcinoma-primary (KC-23) | 0 | 0 | 0 | 0 | 0 |
| Renal Cell Carcinoma-primary (KC-47) | 0 | ● | 0 | 0 | 0 |
| Renal Cell Carcinoma-primary (KC-51) | 0 | 0 | 0 | 0 | 0 |
| Renal Cell Carcinoma-primary (KC-62) | 0 | ● | ● | ● | ● |
| Renal Cell Carcinoma-primary (KC-19) | 0 | 0 | 0 | 0 | 0 |
| Renal Cell Carcinoma-primary (KC-36) | 0 | ●+ | ● | 0 | 0 |
| Renal Cell Carcinoma-primary (KC-44) | 0 | ● | ● | 0 | 0 |
| Renal Cell Carcinoma-primary (KC-52) | 0 | ● | 0 | ● | 0 |
| Renal Cell Carcinoma-primary (KC-66) | 0 | ● | ● | 0 | 0 |
| Renal Cell Carcinoma-primary (KC-10) | 0 | ● | 0 | •● | ● |
| Renal Cell Carcinoma-primary (KC-65) | 0 | ●+ | 0 | 0 | 0 |
| Renal Cell Carcinoma-primary (KC-63) | 0 | ●+ | ● | 0 | 0 |
| Renal Cell Carcinoma-primary (KC-68) | 0 | ● | ● | 0 | 0 |
| Renal Cell Carcinoma-metastatio (KC-7) | 0 | 0 | 0 | 0 | 0 |
| Renal Cell Carcinoma-metastatio (KC-24) | 0 | 0 | 0 | 0 | 0 |
| Renal Cell Carcinoma-metastatio (KC-29) | 0 | ● | 0 | ● | 0 |
| Renal Cell Carcinoma-metastatio (KC-53) | 0 | 0 | 0 | ● | 0 |
| Transitional Cell Carcinoma (Renal pelvis) | 0 | ● | 0 | ● | ● |
| Transitional Cell Carcinoma (Renal pelvis) | 0 | ● | 0 | ● | ● |
| Transitional Cell Carcinoma (Ureter) | 0 | ● | 0 | ● | ● |
| Transitional Cell Carcinoma (Bladder) | 0 | ● | 0 | ● | ● |
| Transitional Cell Carcinoma (Bladder) | 0 | ● | 0 | 0 | ● |
| Transitional Cell Carcinoma (Bladder) | •0 | ● | 0 | .0 | ● |
| Transitional Cell Carcinoma (Bladder) | 0 | ● | 0 | ●' | ● |
| Transitional Cell Carcinoma (Bladder) | 0 | ● | 0 | .● | ●' |
| Adrenal Cortical Carcinoma | 0 | 0 | 0 | 0 | 0 |
| Adrenal Cortical Carcinoma | 0 | 0 | 0 | 0 | 0 |
| Breast Fibroadenoma | 0 | 0 | 0 | ● | 0 |
| Breast Fibroadenoma | 0 | 0 | 0 | ● | ● |
| Breast Adenocarcinoma-primary | 0 | ● | 0 | ● | ●' |
| Breast Adenocarcinoma-primary | 0 | ● | 0 | ● | ●' |
| Breast Adenocarcinoma-metastatic | 0 | ● | 0 | ●' | 0 |
| Colon Adenoma | 0 | ● | 0 | ● | 0 |
| Colon Adenoma | 0 | ● | 0 | ● | 0 |
| Colon Adenocarcinoma | 0 | ● | 0 | ● | 0 |
| Colon Adenocarcinoma | 0 | ● | 0 | ● | 0 |
| Colon Adenocarcinoma | 0 | ● | 0 | ● | 0 |
| Lung Epidermoid Carcinoma | 0 | ● | 0 | ● | 0 |

TABLE IXb-continued

Indirect Immunofluorescence and Immunoperoxidase Analysis of Frozen Sections of Human Tumors and of Cryopreserved Leukemia and Lymphoma Cells.

| Specimens | Monoclonal Antibodies | | | | |
|---|---|---|---|---|---|
| | *Q14 | J143 | AJ8 | C26 | T16 |
| Lung Epidermoid Carcinoma | 0 | ● | 0 | ● | ● |
| Lung Oat Cell Carcinoma | 0 | ● | 0 | ● | 0 |
| Lung Carcinoid | 0 | 0 | 0 | ● | ● |
| Ovarian Carcinoma | 0 | 0 | 0 | ● | 0 |
| Ovarian Carcinoma | 0 | 0 | 0 | ● | ● |
| Ovarian Carcinoma | 0 | 0 | 0 | ● | ● |
| Ovarian Carcinoma | 0 | 0 | 0 | ● | ●' |
| Ovarian Carcinoma | 0 | 0 | 0 | ● | ● |
| Prostatic Adenocarcinoma | 0 | '0 | 0 | ● | 0 |
| Liposarcoma | 0 | 0 | 0 | ● | ● |
| Leiomyosarcoma | 0 | 0 | 0 | 0 | 0 |
| Leiomyosarcoma | ● | 0 | 0 | 0 | 0 |
| Rhabdomyosarcoma (Embryonal) | ● | 0 | 0 | 0 | 0 |
| Rhabdomyosarcoma | 0 | 0 | 0 | 0 | 0 |
| Fibrosarcoma | ● | 0 | 0 | 0 | 0 |
| Chondrosarcoma | 0 | 0 | 0 | 0 | 0 |
| Chondrosarcoma | 0 | 0 | 0 | 0 | 0 |
| Chondrosarcoma | 0 | 0 | 0 | 0 | 0 |
| Osteogenic Sarcoma | 0 | 0 | 0 | 0 | 0 |
| Sarcoma (Spindle Cell) | 0 | 0 | 0 | 0 | 0 |
| Mesothelioma (Lung) | 0 | 0 | 0 | 0 | 0 |
| Astrocytoma-stage I | 0 | 0 | 0 | 0 | 0 |
| Astrocytoma-stage III | 0 | 0 | 0 | 0 | 0 |
| Nevus | 0 | 0 | 0 | •0 | 0 |
| Melanoma-primary | ● | 0 | 0 | 0 | 0 |
| Melanoma-primary | ● | 0 | 0 | 0 | 0 |
| Melanoma-metastatic | 0 | 0 | 0 | 0 | 0 |
| Melanoma-metastatic | ● | 0 | 0 | 0 | 0 |
| Melanoma-metastatic | 0 | 0 | 0 | 0 | 0 |
| Germ Cell Tumor (Embryonal) | ● | 0 | 0 | 0 | 0 |
| Germ Cell Tumor (Embryonal) | 0 | ● | 0 | ● | 0 |
| Germ Cell Tumor (Seminoma) | 0 | 0 | 0 | 0 | 0 |
| B Cell Leukemia | 0 | 0 | 0 | 0 | 0 |
| B Cell Leukemia | 0 | 0 | 0 | 0 | 0 |
| T Cell Leukemia | 0 | 0 | 0 | 0 | 0 |
| T Cell Leukemia | ●' | 0 | 0 | 0 | 0 |
| Null Cell Leukemia | ● | 0 | 0 | 0 | 0 |
| Null Cell Leukemia | 0 | 0 | ● | 0 | 0 |
| Null Cell Leukemia | ● | 0 | ●' | 0 | 0 |
| Acute Myelogenous Leukemia | 0 | 0 | 0 | 0 | 0 |
| Acute Myelogenous Leukemia | 0 | 0 | 0 | 0 | 0 |
| B Cell Lymphoma | 0 | 0 | ● | 0 | 0 |
| B Cell Lymphoma | 0 | 0 | 0 | 0 | 0 |
| T Cell Lymphoma | ● | 0 | 0 | 0 | 0 |

Legend: ●: Strong fluorescence (++++ to ++), ●' weak fluorescence (+), 0 no fluorescence or ●:heterogeneous pattern or ●+ basement membrane pattern of antigen expression.
*Q14 is detected in smooth muscle and vessel matrix of tumors.

What is claimed is:

1. A panel of monoclonal antibodies for determining types of renal cancer consisting of the monoclonal antibodies S4 (ATCC HB 8541), AJ8 (ATCC HB 8339), F23 (ATCC HB 8231), S23 (ATCC HB 8540), S27 (ATCC HB 8428), C26 (ATCC HB 8247), T16 (ATCC HB 8279), S22 (ATCC HB 8542), J143 (ATCC HB 8276), and V1 (ATCC HB 8424).

2. A method for determining types of renal cancers which comprises: (a) contacting a suspected human renal cancer specimen with the panel of claim 1; and (b) detecting whether a reaction occurs between the specimen and the panel, and thereby determining the types of renal cancer.

3. A panel of monoclonal antibodies for determining types of renal cancer consisting of the monoclonal antibodies S4 (ATCC HB 8541), AJ8 (ATCC HB 8339), F23 (ATCC HB 8231), S23 (ATCC HB 8540), S27(ATCC HB 8428), C26 (ATCC HB 8247), T16 (ATCC HB 8279), and S22 (ATCC HB 8542).

4. A method for determining types of renal cancer which comprises (a) contacting a suspected human renal cancer specimen with the panel of claim 3; and (b) detecting whether a reaction occurs between the specimen and the panel, and thereby determining the types of renal cancer.

5. A panel of monoclonal antibodies for determining types of renal cancer consisting of the monoclonal antibodies S4 (ATCC HB 8451), F23 (ATCC HB 8231), S23 (ATCC HB 8540), S27 (ATCC HB 8428), S22 (ATCC HB 8542), and V1 (ATCC HB 8424).

6. A method for determining types of renal cancer which comprises (a) contacting a suspected human renal cancer specimen with the panel of claim 5; and (b) detecting whether a reaction occurs between the specimen and the panel, and thereby determining the types of renal cancer.

* * * * *